(12) United States Patent
Wilkes et al.

(10) Patent No.: US 8,880,354 B2
(45) Date of Patent: Nov. 4, 2014

(54) SYSTEM FOR MAGNETIC RESONANCE SPECTROSCOPY OF BRAIN TISSUE FOR PATTERN-BASED DIAGNOSTICS

(75) Inventors: Jon G. Wilkes, Little Rock, AR (US); Dan A. Buzatu, Benton, AR (US); Pierre Alusta, Little Rock, AR (US); Bruce Pearce, White Hall, AR (US); Ryan M. Kretzer, Baltimore, MD (US); Inessa Im, Little Rock, AR (US); Richard D. Beger, White Hall, AR (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/509,539

(22) PCT Filed: Nov. 12, 2010

(86) PCT No.: PCT/US2010/056486
§ 371 (c)(1),
(2), (4) Date: Aug. 6, 2012

(87) PCT Pub. No.: WO2011/060237
PCT Pub. Date: May 19, 2011

(65) Prior Publication Data
US 2013/0131992 A1    May 23, 2013

Related U.S. Application Data

(60) Provisional application No. 61/261,170, filed on Nov. 13, 2009.

(51) Int. Cl.
*G01N 33/48* (2006.01)
*G06F 19/00* (2011.01)
*G01R 33/46* (2006.01)

(52) U.S. Cl.
CPC ............ *G06F 19/36* (2013.01); *G01R 33/4625* (2013.01)
USPC .......................................................... 702/19

(58) Field of Classification Search
None
See application file for complete search history.

(56) References Cited

PUBLICATIONS

M.Martinez-Hisbal, et al., IH and 13C HR-MAS spectroscopy of intact biopsy samples ex vivo and in vivo 1H MRS study of human high grade gliomas, NMR Biomed., 2004;17:191-205.
P.B.Webb et al., Automated single-voxel proton MRS: technical development and multisite verification, Magn. Reson. Med., 1994;31:365-73.

*Primary Examiner* — Eric S Dejong
(74) *Attorney, Agent, or Firm* — Polsinelli PC; Teddy C. Scott, Jr.; Ron Galant

(57) ABSTRACT

A system and method for preprocessing magnetic resonance spectroscopy (MRS) data of brain tissue for pattern-based diagnostics is disclosed. The MRS preprocessing system includes an MRS preprocessing module that executes an operation that normalizes MRS spectrum data, recalibrates and scales the normalized MRS spectrum data, and then renormalizes the scaled MRS spectrum data. The resulting preprocessed MRS data is used to assist in identifying abnormalities in tissues shown in MRS scans.

8 Claims, 16 Drawing Sheets

SYSTEM FOR MAGNETIC RESONANCE SPECTROSCOPY OF BRAIN TISSUE FOR PATTERN-BASED DIAGNOSTICS

CROSS-REFERENCE TO RELATED APPLICATIONS

This is the national stage of International Application No. PCT/US2010/056486, filed on Nov. 12, 2010, which claims the benefit of U.S. Provisional Patent Application No. 61/261,170, filed on Nov. 13, 2009, the contents of all of which are hereby incorporated herein by reference.

FIELD

This document relates to magnetic resonance spectroscopy ("MRS"), and in particular a system and method for pre-processing MRS data of brain tissue for pattern-based diagnostics.

BACKGROUND

The diagnosis of brain tissue anomalies is an ongoing challenge in modern medicine. Because of the location of the brain within the skull, and the sensitivity of brain tissue to invasive procedures, the diagnosis of suspected brain disease balances the need for timely and accurate diagnosis with the need to minimize damage to the brain tissue in the course of performing diagnostic procedures. The risk of adverse outcomes related to the diagnostic procedures is significant. For example, in 7,500 brain biopsy procedures conducted from 1979 to 1991, the diagnostic accuracy was 91%. However, the morbidity and mortality rates associated with the invasive biopsy procedure were 3.5% and 0.7%, respectively.

In addition, early detection leading to early intervention in a brain anomaly is an important consideration. However, due to the dangers associated with biopsy in a situation of recognized tissue anomaly, early detection is typically achieved using non-invasive procedures such as computed tomography (CT) or magnetic resonance imaging (MRI). However, existing non-invasive diagnostic procedures are relatively ineffective at detecting the early stages of a brain anomaly. Based on non-invasive procedures such as CT or MRI scans alone, practitioners cannot consistently distinguish radiation necrosis or benign lesions from malignant tumors.

Magnetic resonance spectroscopy (MRS) with pattern recognition has recently shown potential for the non-invasive diagnosis of brain lesions, for direction of surgical or other therapeutic interventions, and for determining prognosis. Patterns indicative of abnormal tissue appear in brain MRS scans before any abnormality is indicated in the corresponding MRI scans. Therefore, use of reliable MRS-based patterns could enable earlier detection of brain tissue anomalies. Further, if the MRS scans contain sufficiently distinctive and reliable markers, MRS diagnostic procedures could augment or substitute for histological grading, guide surgical intervention at tumor margins and areas of local invasion, and monitor radiation or chemo-therapy progress. Whether these potential advantages are realized depends on the predictive quality of computational models based on MRS scan data that in turn depend on the consistency and inherent informational content of the MRS scans.

Previous research on a variety of tissue types indicates that 1.5 Tesla (T) MRS scans contain information useful for diagnostic purposes, particularly biomarkers for AT-acetyl aspartate (NAA), choline (Cho), creatinine (Cr), myo-inositol (MI), lactate, and lipids. For example, using an automated two-category classification model, MRS diagnostic procedures achieved a sensitivity of 80% and specificity of 86% for discriminating breast cancer tissue from scar tissue. However, in brain or other tissues, simple biomarker ratios used for diagnosis such as Cho/Cr cannot adequately distinguish malignant lesions from other features such as progressive multifocal leukoencephalopathy, multiple sclerosis, stroke, and scar tissue.

The detection of brain lesions using MRS requires recognizing patterns in MRS scans associated with abnormalities. One method involves the interpretation of MRS scan patterns by an expert practitioner. When an expert interprets MRS spectra for diagnostic purposes, he/she may consider the relative amounts or ratios of two or three biomarkers such as Cho/Cr. Spectrum scans are visually examined, peak biomarkers are identified, and peak heights are scaled manually to determine these ratios. MRS peaks, even if not precisely at the expected chemical shift, may be recognized for the biomarker they represent by the relationship of the biomarker peak to the familiar pattern of peaks in the MRS scan.

Diagnostic pattern recognition on the whole MRS spectrum, rather than classification based on a few biomarker ratios, is a recent development. The effective use of multiple biomarkers for diagnosis requires not expert, but automated peak identification and quantification. For example, a multi-center study evaluated automated classification of tumors based on proton MRS patterns using linear discriminant analysis and leave-one-out validation to achieve greater than 90% correct classification of the tissue type in scans from multiple instruments and centers. However, the classification scheme of this study was limited to only three types of tumors. In routine practice, the accurate diagnosis of many different types of tumors as well as normal tissue and other types of non-cancerous anomalies is highly desirable. This goal may be achieved using MRS scans of normal tissue and other types of non-cancerous anomalies in the training and external validation sets of an automated diagnostic pattern recognition method. The accuracy and utility of predictive models strongly depend on at least several factors related to the quality of the MRS scans such as the reproducibility of chemical shifts for each biomarker and the potential for confusion among the spectrum classes modeled.

For example, spatial variation in $B_o$, the magnetic field strength of the MRS devices, may result in the misalignment of biomarker chemical shifts. The magnetic field strength varies as a function of target tissue depth. Although the scale of the variations in chemical shift is not so great as to cause misidentification of markers under expert interpretation, the same is not true when automated detection of many different biomarkers is required for computerized pattern recognition. Misidentification of biomarkers between data replicates confounds the MRS-based models and effectively decreases peak resolution by spreading the domain over which each diagnostic feature may appear. For example, FIG. 1 shows an example of the variation in biomarker chemical shifts among several spectra measured from the same tissue type.

The non-uniformity of biomarker peaks represents a significant limitation in use of automated MRS-based pattern recognition. High-magnetic-field medical MRI devices produce MRS scans that have greater biomarker peak resolution and therefore superior ability to distinguish proximate, but diagnostically distinct, spectrum features. For example, using a high-powered 8.5 T MRS device to analyze tissue samples from fine needle biopsies, breast tissue anomalies were detected with nearly 100% correct categorization and sensitivity for the extent of breast tissue anomalies. However, the high-powered MRS instruments are not nearly as ubiquitous as 1.5 T MRS instruments in the medical community.

Another approach to enhancing the quality of MRS data is the preprocessing of the raw MRS data prior to analysis. Data preprocessing is a well-known tool used in research fields that utilize high volumes of data containing both signal and noise, such as mass spectrometry, genomics, proteomics, metabolomics, and structure-activity relationships. Common preprocessing techniques typically include normalization, baseline correction, various kinds of weighting, smoothing, variance or other kinds of scaling, and a priori information weighting. In all computational modeling, such as that used for MRS pattern recognition, there is a concern that preprocessing may obscure the informational content of the raw data; validation of the model and its predictions is important in order to assess the value of preprocessing steps.

Previous research has highlighted the beneficial effects of preprocessing MRS data using normalization and digitization on the diagnostic outcome of predictive diagnostic models. However, research to date has overlooked the importance of re-calibrating MRS spectra to account for $B_o$ variations in order to realign the chemical shifts as a critical first step in data preprocessing. A need exists in the art for a preprocessing method that minimizes variation in chemical shifts and enhances the resolution of biomarker shifts relative to random noise. Due to the higher consistency of the preprocessed MRS relative to the raw MRS scans, higher resolution of tissue types including healthy tissue, non-malignant tumors, and different types of tumors could be achieved. Further, the higher fidelity signal even when the MRS signal is relatively weak resulting from preprocessing would make possible the earlier detection of tissue anomalies. In addition, preprocessing of MRS data measured using the more commonly available lower-powered MRS devices would make the enhanced diagnostic methodologies using automated MRS pattern detection more widely available.

SUMMARY

In an embodiment, a method for preprocessing Magnetic Resonance Spectroscopy (MRS) spectrum data may include the steps of providing a raw MRS spectrum data and scaling the raw MRS spectrum data by using a plurality of weighting constants to generate a preprocessed MRS spectrum data.

In another embodiment, a method for preprocessing Magnetic Resonance Spectroscopy (MRS) spectrum data may include the steps of: providing a database including raw MRS spectrum data, defined herein as a frequency-domain spectrum resulting from a Fourier transform of a set of free induction decay (FID) data collected by the MRS instrument for a particular tissue sample. The method may further include normalizing the raw spectrum data to generate normalized MRS spectrum data, scaling the normalized MRS spectrum data by using a plurality of weighting constants to generate a weighted MRS spectrum data, and renormalizing the weighted MRS spectrum data to generate a preprocessed MRS spectrum data.

In an embodiment, a method for preprocessing MRS spectrum data includes providing a raw MRS spectrum data, recalibrating the raw MRS spectrum data, and scaling the recalibrated MRS spectrum data by using a plurality of weighting constants to generate a preprocessed MRS spectrum data.

In yet another embodiment, a method for preprocessing MRS spectrum data may include the steps of: providing a database having raw MRS spectrum data, normalizing the raw spectrum data to generate normalized MRS spectrum data, scaling the normalized MRS spectrum data by using a plurality of weighting constants to generate a weighted MRS spectrum data, and renormalizing the weighted MRS spectrum data to generate a preprocessed MRS spectrum data.

In one embodiment, an MRS preprocessing system for preprocessing raw MRS spectrum data may include one or more processors and a plurality of modules configured to be executed by the one or more processors. The plurality of modules may include a normalization module to normalize the raw MRS spectrum data to generate normalized MRS spectrum data. In addition, a recalibration module shifts each of the nuclear magnetic resonance frequencies representing a particular biomarker to a reference nuclear magnetic resonance frequency representing the particular biomarker to generate a recalibrated MRS spectrum data. A variance-weighting module scales the recalibrated MRS spectrum data by using a plurality of weighting constants to generate a weighted MRS spectrum data. Finally, a renormalization module renormalizes the weighted MRS spectrum data to generate a preprocessed MRS spectrum data.

In yet another embodiment, a machine-readable media may be encoded with an MRS preprocessing system to process raw MRS spectrum data. The MRS preprocessing system may include machine readable instructions executable by at least one processor to perform the steps of: receiving raw MRS spectrum data at the MRS preprocessing system executing on at least one processor, normalizing the raw MRS spectrum data to generate normalized MRS spectrum data, scaling the normalized MRS spectrum data by using a plurality of weighting constants to generate a weighted MRS spectrum data, and renormalizing the weighted MRS spectrum data to generate a preprocessed MRS spectrum data.

In a further embodiment, a machine-readable media may be encoded with an MRS preprocessing system to process raw MRS spectrum data, the MRS preprocessing system comprising machine readable instructions executable by at least one processor to perform the steps of receiving raw MRS spectrum data at the MRS preprocessing system executing on at least one processor; normalizing the raw MRS spectrum data to generate normalized MRS spectrum data; recalibrating the normalized MRS spectrum data; scaling the recalibrated MRS spectrum data by using a plurality of weighting constants to generate a weighted MRS spectrum data; and renormalizing the weighted MRS spectrum data to generate a preprocessed MRS spectrum data.

In one embodiment, a method for detecting tissue abnormalities may include the steps of: providing a database including a raw MRS spectrum data, normalizing the raw spectrum data to generate normalized MRS spectrum data, scaling the normalized MRS spectrum data by using a plurality of weighting constants to generate a weighted MRS spectrum data; and renormalizing the weighted MRS spectrum data to generate a preprocessed MRS spectrum data, whereby the preprocessed MRS spectrum data provides a means for detecting tissue abnormalities for pattern recognition diagnostics of a tissue at an accuracy rate of at least 90%.

A method for preprocessing MRS spectrum data may include providing a database having a raw MRS spectrum data. The raw spectrum data includes a summary of the signals produced by a tissue sample at a range of nuclear magnetic resonance frequencies with each of the raw spectrum data including one or more Nuclear Magnetic Resonance (NMR) frequencies and corresponding signals measured from the tissue at each NMR frequency, wherein each NMR frequency is provided in the form of a chemical shift, the chemical shift being the percentage shift in a particular NMR frequency relative to the NMR frequency of a reference chemical. The raw spectrum data is normalized to generate normalized MRS spectrum data, and then the normalized MRS spectrum data is scaled using a plurality of weighting constants to generate a weighted MRS spectrum data. Finally, the weighted MRS spectrum data is renormalized to generate a preprocessed MRS spectrum data with the preprocessed MRS spectrum data having a value range from a minimum value of 0 to a maximum value of 1.

In one embodiment, a method for detecting a tissue abnormality may include providing a preprocessed MRS spectrum data of a tissue sample made up of a summary of signals produced by the tissue sample at a range of nuclear magnetic resonance frequencies. In addition the preprocessed MRS spectrum data of the tissue sample may include a raw MRS spectrum data subjected to a preprocessing method including normalization, recalibration, scaling by variance-weighting, and renormalization. The method also may include providing a set of preprocessed comparison MRS spectrum data that may include a plurality of preprocessed comparison MRS spectrum data, where each preprocessed comparison MRS spectrum data of the set may include a summary of signals produced by an abnormal tissue sample having a known abnormality at a range of nuclear magnetic resonance frequencies. Further, each preprocessed comparison MRS spectrum data of the set may include a raw comparison MRS spectrum data subjected to a preprocessing method including normalization, recalibration, scaling by variance-weighting, and renormalization. The method may also include comparing the preprocessed MRS spectrum data of the tissue sample to the set of preprocessed comparison MRS spectrum data using a pattern recognition method and identifying the tissue abnormality as the known abnormality of the preprocessed comparison MRS spectrum data that most closely matches the preprocessed MRS spectrum data of the tissue sample.

In another embodiment, a method for detecting a tissue abnormality may include providing a preprocessed MRS spectrum data of a tissue sample made up of a summary of signals produced by the tissue sample at a range of nuclear magnetic resonance frequencies. In addition the preprocessed MRS spectrum data of the tissue sample may include a raw MRS spectrum data subjected to a preprocessing method including normalization, recalibration, scaling by variance-weighting, and renormalization. The method also may include providing a set of preprocessed comparison MRS spectrum data that may include a plurality of preprocessed comparison MRS spectra data, where each preprocessed comparison MRS spectrum data of the set may include a summary of signals produced by an abnormal tissue sample having a known abnormality at a range of nuclear magnetic resonance frequencies. Further, each preprocessed comparison MRS spectrum data of the set may include a raw comparison MRS spectrum data subjected to a preprocessing method including normalization, recalibration, scaling by variance-weighting, and renormalization. The method may further include forming a tissue biomarker signal group that may include at least one of the summary of signals produced by the tissue sample at a particular nuclear magnetic resonance frequency representing a particular biomarker and forming a set of comparison tissue biomarker signal groups, where each comparison tissue biomarker signal group of the set may include at least one of the summary of signals produced by an abnormal tissue sample having a known abnormality at a particular nuclear magnetic resonance frequency representing the same particular biomarker as the particular biomarker of the tissue biomarker signal group. The method may also include comparing the tissue biomarker signal group to the set of comparison tissue biomarker signal groups using a pattern recognition method and identifying the tissue abnormality as the known abnormality of the comparison tissue biomarker signal group most closely matching the tissue biomarker signal group of the tissue sample.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
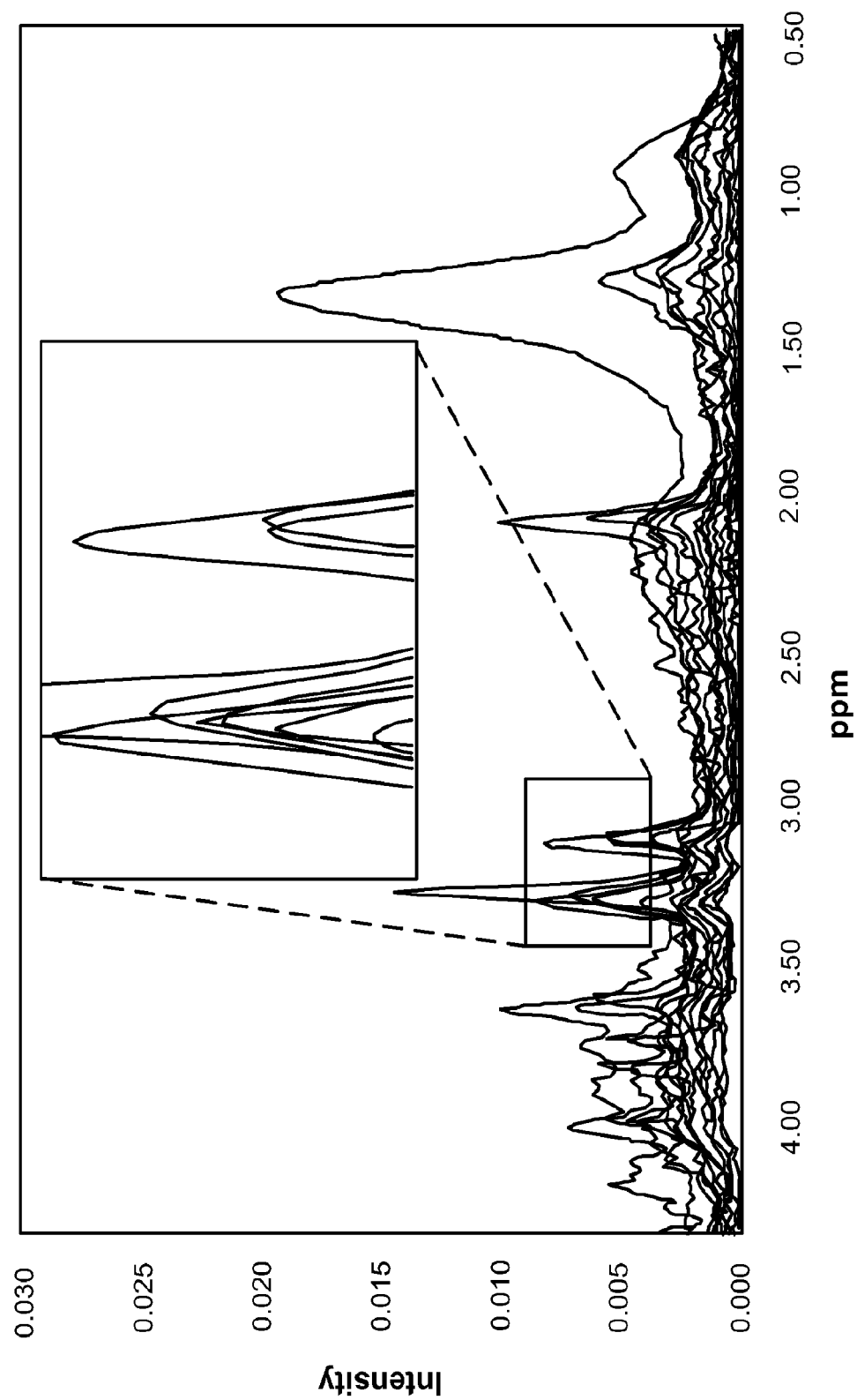
FIG. 1 is a graph of the MRS spectra of 24 oligodendroglioma tissue samples.

A Magnetic Resonance Spectroscopy (MRS) preprocessing system is provided that processes MRS spectrum data that includes an array of chemical shift values and corresponding signal values. The preprocessed MRS spectrum data may be subsequently analyzed using techniques including but not limited to visual inspection by an expert practitioner and automated pattern recognition diagnostic systems. Because the MRS preprocessing system compensates for the confounding effects including but not limited to magnetic field heterogeneity in the MRS device and random noise, a much higher efficacy of automated pattern recognition diagnostic methods may be achieved. The preprocessing methods implemented by the MRS preprocessing system may include a chemical shift recalibration in which the chemical shifts in the MRS spectrum data may be adjusted based on the alignment of selected chemical shifts in the MRS spectrum data to coincide with the previously determined chemical shifts of known biomarkers. Another method that may be optionally implemented by the MRS preprocessing system is a variance-weighting method, in which the signal values at chemical shifts corresponding to frequently observed biomarker peaks may be enhanced relative to the signal values at chemical shifts corresponding to random noise, in which relatively few biomarker peaks are observed.

Referring to the drawings, a non-limiting exemplary embodiment of an MRS preprocessing system is illustrated and generally indicated as 100 in FIGS. 2-13. MRS spectrum data may include one or more signals paired with a corresponding NMR frequency. The signal may correspond to an amount of energy released by charged particles including but not limited to protons in a tissue sample in response to the absorption of applied electromagnetic pulses. The NMR frequency is defined herein as the resonant frequency of an applied electromagnetic pulse used to generate a signal. The various embodiments of the MRS preprocessing system 100 may provide a means for preprocessing raw MRS spectrum data 101 for the detection of tissue abnormalities using methods including but not limited to pattern recognition diagnostics of tissue. Raw MRS spectrum data 101, as defined herein, is a summary of the signals produced by a tissue sample at a range of different nuclear magnetic resonance frequencies. Each of the spectra in the raw MRS spectra data 101 may include one or more NMR frequencies and the corresponding signals measured from the sample at each NMR frequency. The NMR frequency may be provided in the form of a chemical shift, defined herein as the percentage shift in NMR frequency relative to the NMR frequency of a reference chemical, expressed in parts per million (ppm). In the context of this application, the terms "chemical shift" and "NMR frequency" may be used interchangeably. Biomarkers contained in the sample typically produce a strong signal at a characteristic chemical shift, thereby may result in an identifiable signal peak at the biomarker's characteristic chemical shift.

The preprocessed MRS spectrum data 103 resulting from the processing of the raw MRS spectrum data 101 by embodiments of the MRS preprocessing system 100 may be used to diagnose tissue abnormalities by detecting patterns in the chemical shifts of the MRS spectrum. The chemical shift patterns may be detected by implementing an automated pattern detection method by the MRS preprocessing system 100. Because the preprocessed MRS spectrum data 103 may be of a more uniform quality than the raw MRS spectrum data 101, the diagnosis accuracy resulting from preprocessed MRS data 103 may be significantly enhanced relative to the diagnosis accuracy resulting from unprocessed MRS data 101 in various embodiments.

MRS Preprocessing System Overview

Figure 2:
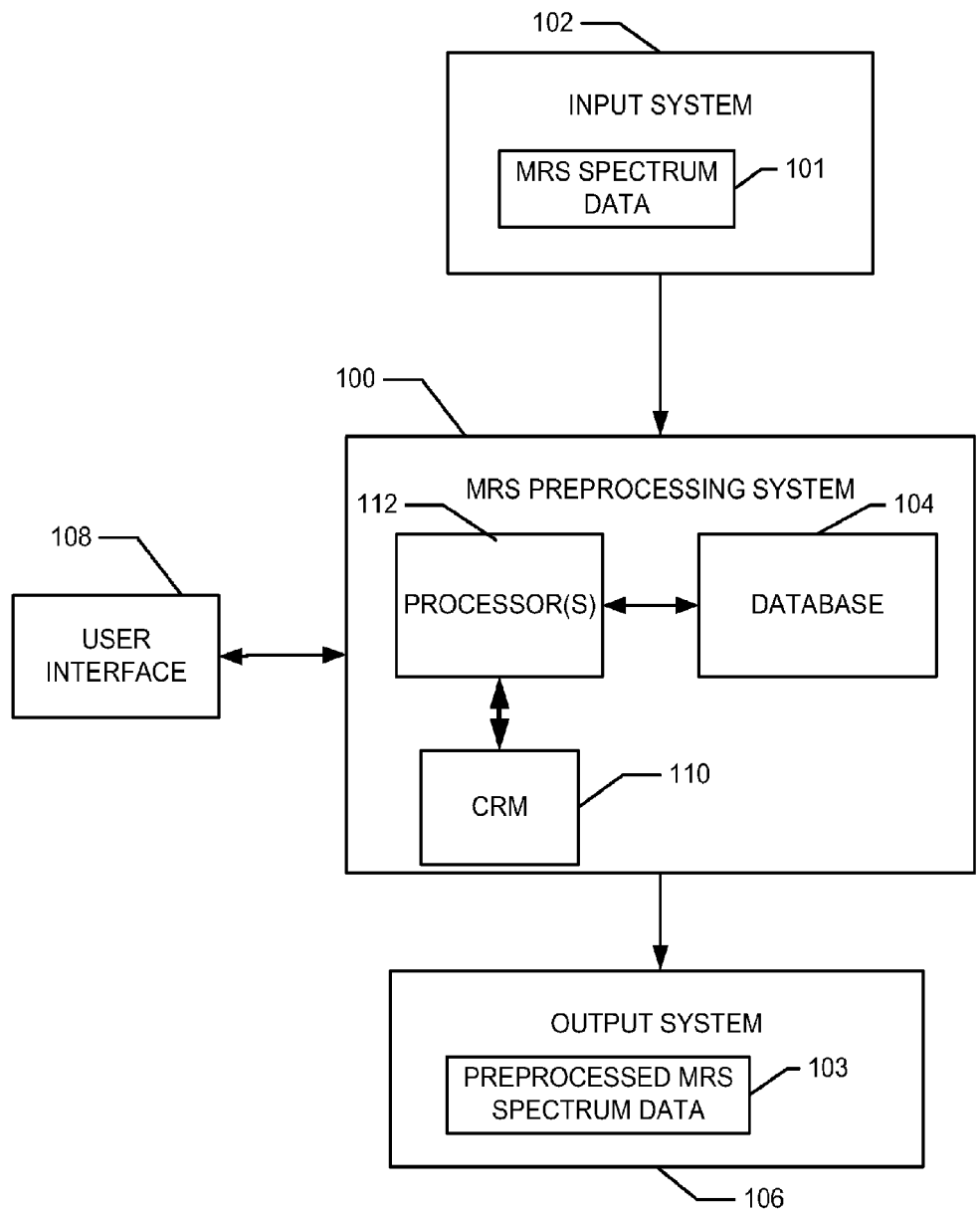
FIG. 2 is a block diagram illustrating a non-limiting exemplary embodiment of an MRS preprocessing system.

Referring to FIG. 2, a non-limiting exemplary embodiment of the MRS preprocessing system 100 may use a combination of chemical shifts and variance weighting for preprocessing raw MRS spectrum data 101 that may be communicated to the MRS processing system 100 by input system 102 or otherwise stored or present in the MRS preprocessing system 100. Input system 102 may include one or more devices or systems used to generate or transfer an electronic version of one or more raw MRS spectrum data 101 to the MRS preprocessing system 100. Once the raw MRS spectrum data 101 is preprocessed by the MRS processing system 100, the preprocessed spectrum data 103 may be passed to an output system 106 for storage and later analysis using a technique including but not limited to known automated pattern recognition diagnostic systems. Alternately, the preprocessed spectra data 103 may stored at the MRS preprocessing system 100. The MRS preprocessing system 100 may also generate information to the user interface 108, including but not limited to the status of the preprocessing process, results, or queries for system input.

In one non-limiting embodiment, the MRS preprocessing system 100 may include one or more processors 112 that may be embodied by or in one or more distributed or integrated components or systems. The MRS preprocessing system 100 may include a database 110 on which data may be stored and a computer readable media (CRM) 104 on which one or more algorithms, software, modules, data, computer readable instructions, and/or firmware may be loaded and/or operated and/or which may operate on the one or more processors 112 to implement the systems and methods identified herein. In an embodiment, the database may be a storage system that temporarily and/or permanently stores data and may include volatile and/or nonvolatile memory and/or other types of storage systems or devices.

MRS Preprocessing System

Figure 3:
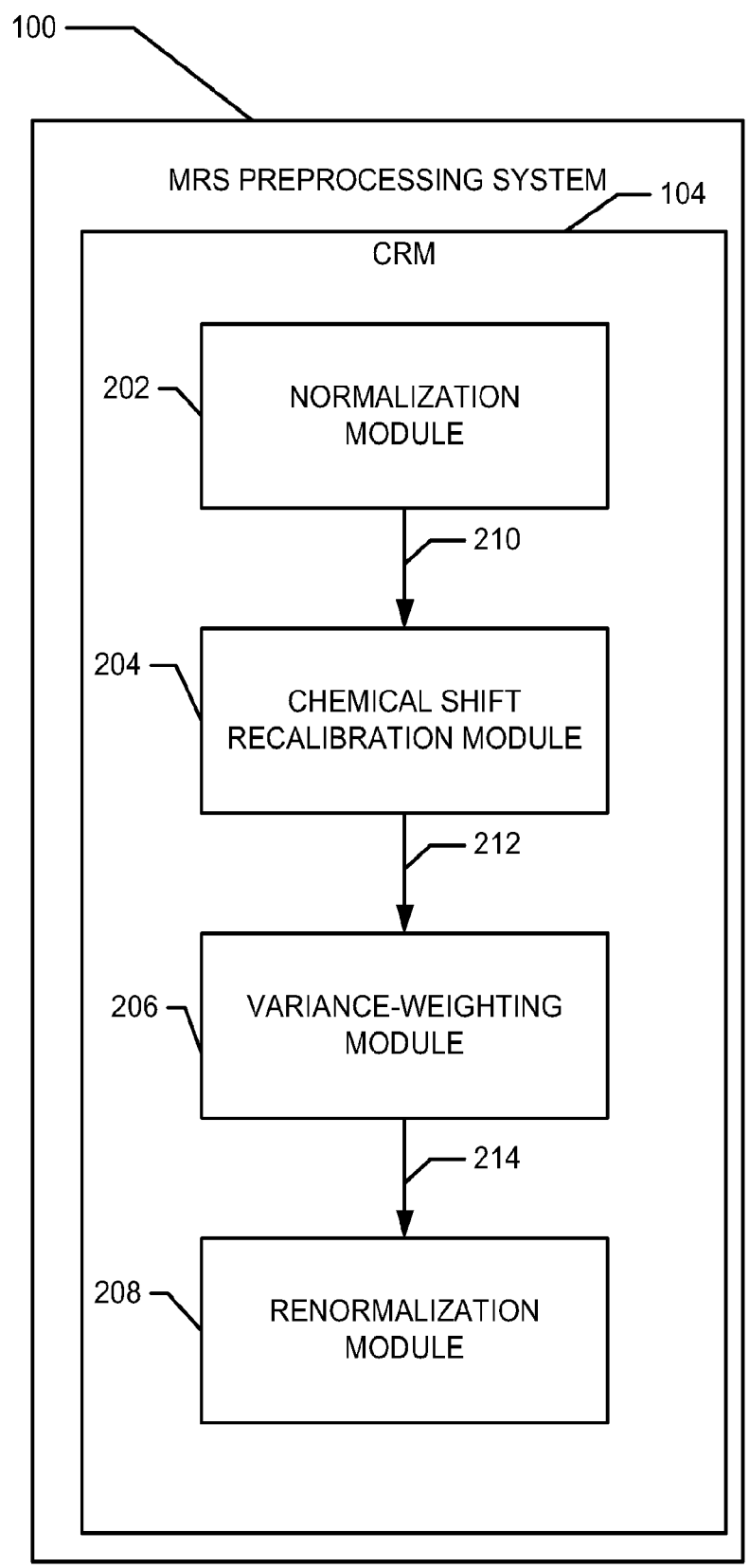
FIG. 3 is a block diagram illustrating a non-limiting exemplary embodiment of an MRS preprocessing system.

Referring to FIG. 3, a block diagram illustrates the modules of a non-limiting exemplary embodiment of the MRS preprocessing system 100 that may execute on the processor 112 to preprocess the raw MRS spectrum data 101. The MRS preprocessing system 100 may include modules including but not limited to a normalization module 202 for normalizing raw MRS spectrum data 101, a chemical shift recalibration module 204 for recalibrating the normalized MRS spectrum data 210, a variance-weighting module 206 for providing a scaling function and scaling the recalibrated MRS spectrum data 212, and a renormalization module 208 that may optionally renormalize the weighted spectrum data 214 as shall be discussed in greater detail below.

The normalization module 202 may process the raw MRS spectrum data 101 and normalize the raw MRS spectrum data 101 such that the signal values at all chemical shifts of the normalized MRS spectrum data 210 may be normalized to values ranging from a normalized minimum value to a normalized maximum value. The chemical shift recalibration module 204 may then recalibrate the normalized MRS spectrum data 210 by re-aligning the chemical shifts corresponding to two or more selected biomarkers to standardized chemical shift values, and may optionally interpolate all remaining chemical shifts in the normalized MRS spectrum data 210 to fall in an even distribution between the two or more re-aligned chemical shifts. The resulting recalibrated MRS spectrum data 212 may be processed by the variance-weighting module 206, which may scale the data 212 at each chemical shift up or down according to a predetermined schedule based on the observed variance of the signals in a set of reference MRS spectra analyzed previously. The variance-weighted MRS spectrum data 214 may optionally be further processed by the renormalization module 208, which may renormalizes the data 214 such that the signal values at all chemical shifts of the renormalized MRS spectrum data 215 range from a normalized minimum value to a normalized maximum value. The renormalized MRS spectrum data 215 may be passed to the output system 106 for analysis by techniques including but not limited to visual inspection by an expert practitioner or automated pattern recognition techniques.

Normalization Module

Figure 4:
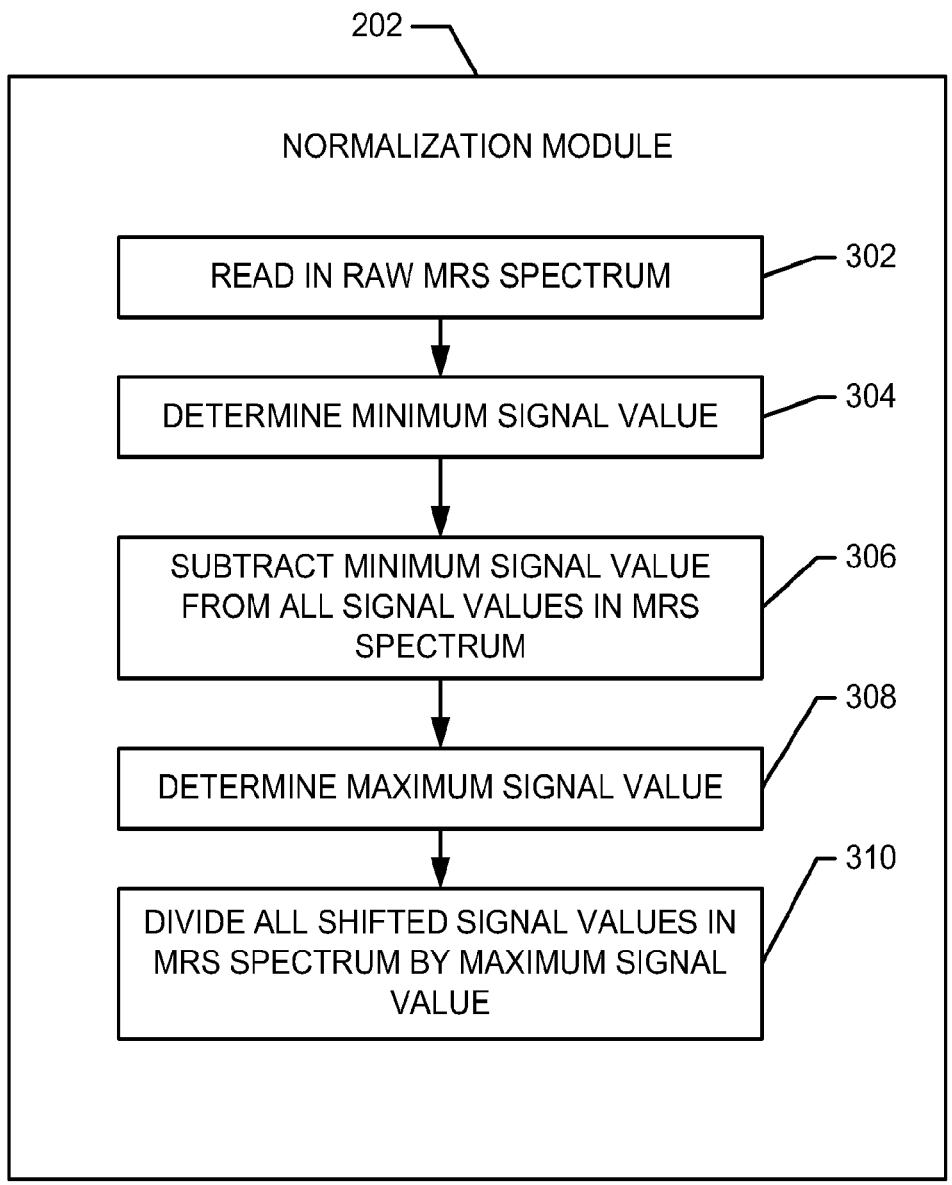
FIG. 4 is a flow chart of the processes of a normalization module in a non-limiting exemplary embodiment of an MRS preprocessing system.

Referring to FIG. 4, a flow chart illustrates the operation of a non-limiting exemplary embodiment of a normalization module 202. The normalization module 202 may process raw MRS spectrum data 101, which may include a summary of at least one signal, a minimum signal value, and a maximum signal value. The normalization module 202 may transform all signal values of the raw spectrum data to values ranging from a normalized minimum value to a normalized maximum value range. One non-limiting example of a normalized minimum value is 0, and one non-limiting example of a normalized maximum value is 1. At step 302, the normalization module 202 may access the raw MRS spectrum data 101, which may be stored on the input system 102. In this non-limiting exemplary embodiment, the normalization module 202 may determine a minimum signal value of all the signal values in the spectrum at step 304 and may subtract the minimum signal value from all signal values in the MRS spectrum at step 306 to generate a shifted signal. In this embodiment, the shifted signal values of the MRS spectrum may range between a signal value of 0 at the same chemical shift at which the minimum value was determined in step 304 and a maximum signal value. This maximum signal value may be determined in step 308, and all shifted signal values may be divided by this maximum signal value at step 310 to produce the normalized MRS spectrum data 210.

Chemical Shift Recalibration Module

Figure 5:
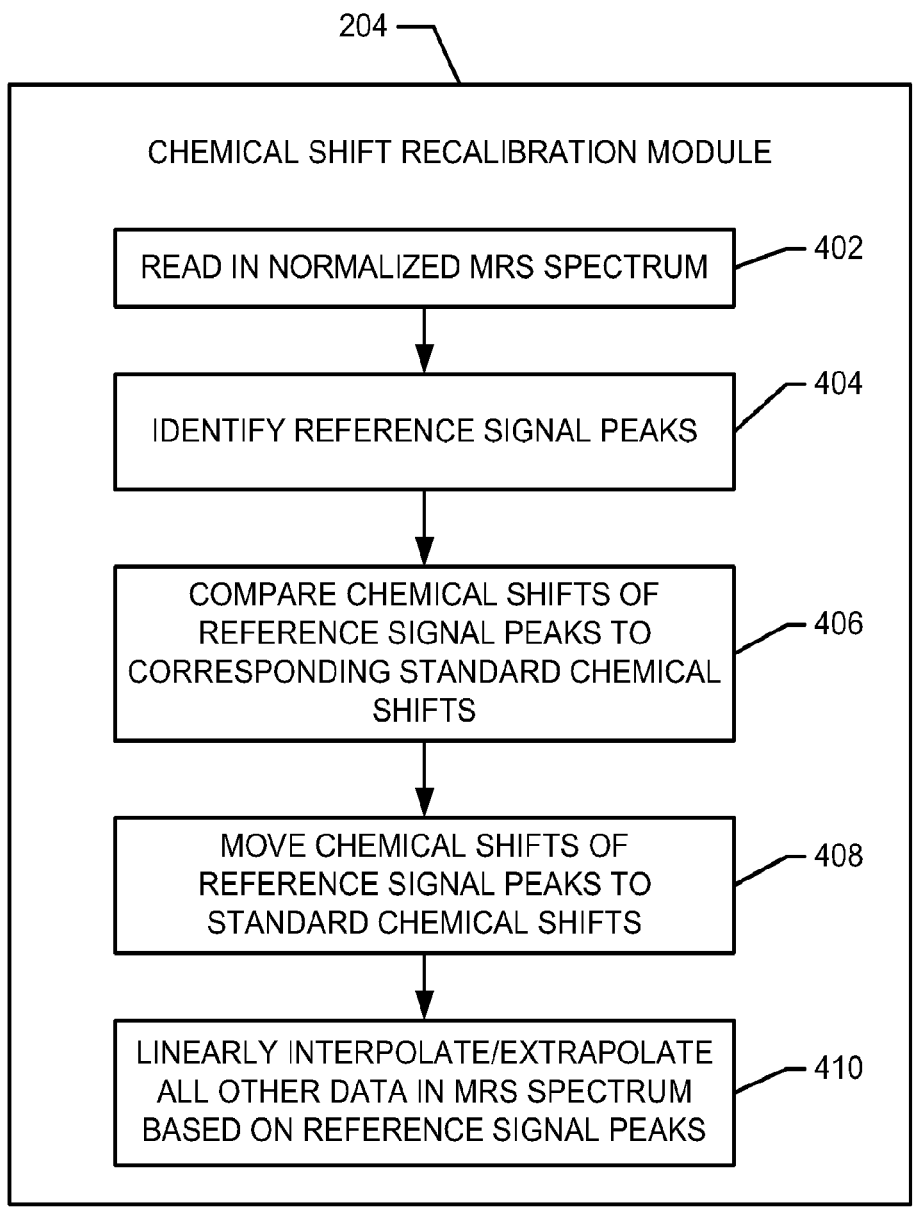
FIG. 5 is a flow chart of the processes of a chemical shift recalibration module in a non-limiting exemplary embodiment of an MRS preprocessing system.
Figure 6:
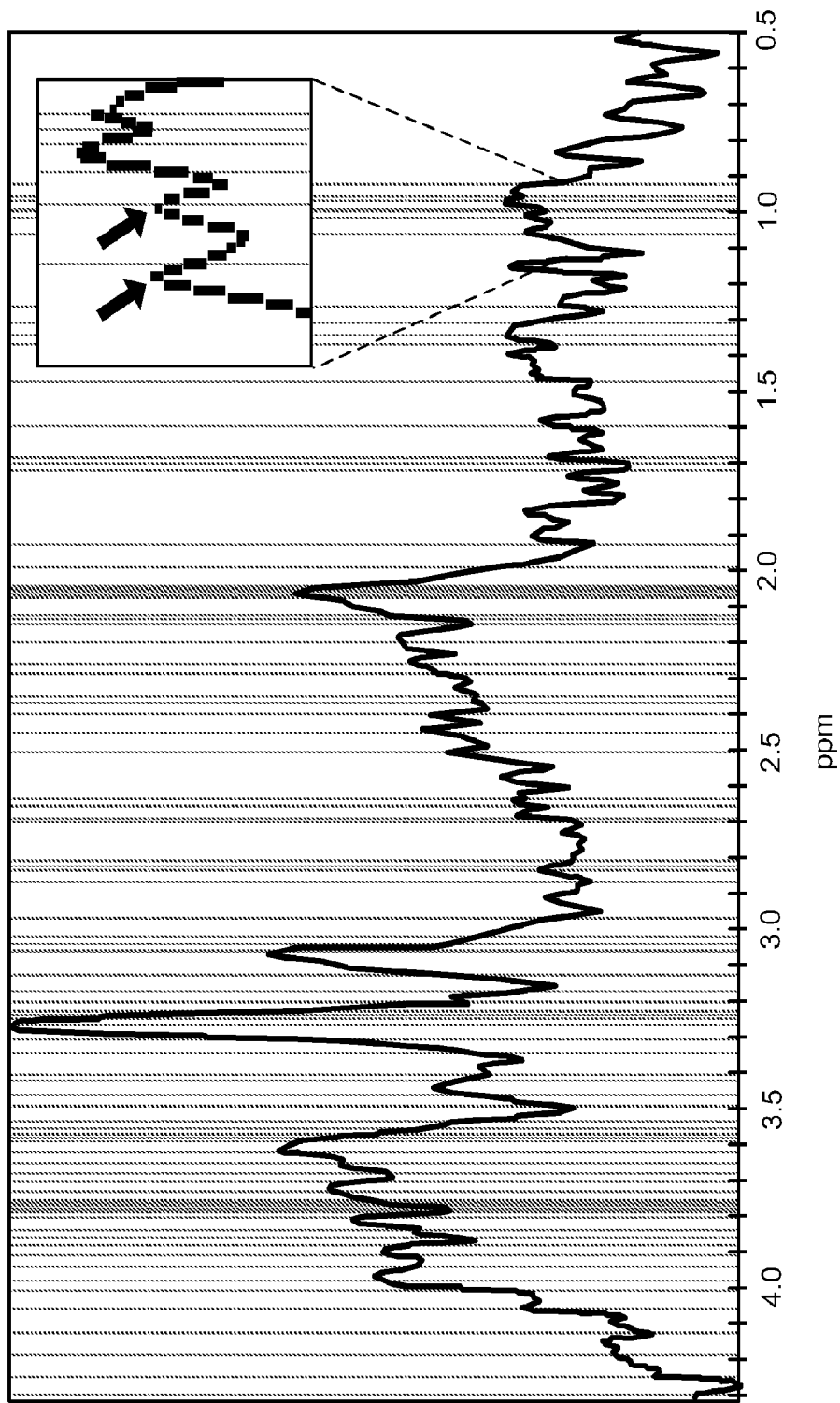
FIG. 6 is a graph showing an MRS spectrum of astrocytoma tissue overlaid with previously reported biomarker locations.

FIG. 5 is a flow chart illustrating the operation of one non-limiting exemplary embodiment of the chemical shift recalibration module 204. The chemical shift recalibration module 204 may recalibrate the normalized MRS spectrum data 210 by shifting each of the nuclear magnetic resonance frequencies representing a particular biomarker to a reference nuclear magnetic resonance frequency representing the same particular biomarker. At step 402, the chemical shift recalibration module 204 may process the normalized MRS spectrum data 210 and corrects the chemical shifts of the data 210 to compensate for magnetic field non-homogeneity in the MRS apparatus (not shown). Referring back to FIG. 5, two or more reference signal peaks may be identified in the normalized MRS spectrum data 210 at step 404. Reference signal peaks, as defined herein, are signal peaks corresponding to known biomarkers. For example, FIG. 6 shows a non-limiting example of an MRS spectrum on which 97 previously documented biomarker peaks (Martinez-Bisbal et al, 2004) have been overlaid.

In one embodiment, the reference signal peaks representing particular biomarkers may be identified by inspection of the raw MRS spectrum data 101 by an expert practitioner. In another embodiment, the reference signal peaks may be identified using an automated identification method. The reference signal peaks may be identified by the presence of a signal peak in close proximity to a previously documented chemical shift of a known biomarker's signal peak in another embodiment. In still another embodiment, the reference signal peaks may be identified by the presence of the peak at a relative position within a previously documented pattern of signal peaks.

The chemical shift location of reference signal peaks in the normalized MRS spectrum data 210 may be compared to the previously documented standard chemical shifts at step 406, and the chemical shifts of the reference signal peaks in the normalized MRS spectrum data 210 may be moved to coincide with the standard chemical shifts at step 408 to generate the recalibrated MRS spectrum data 212. In addition, the location of all other chemical shifts in the MRS spectrum may be optionally moved based on a linear interpolation using the newly relocated reference signal peaks identified in step 404, in order to preserve the relative distance of the other chemical shifts relative to the reference signal peaks at step 410.

Figure 7A:
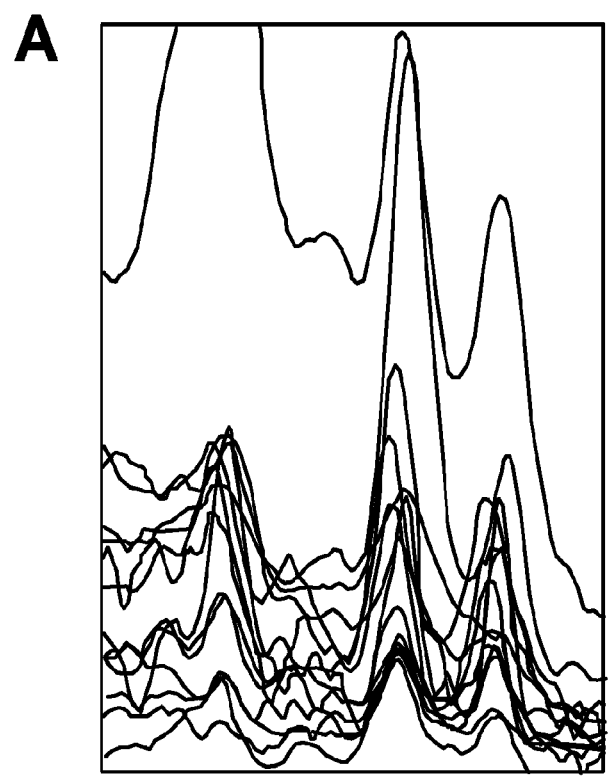
FIG. 7A is a graph comparing fourteen MRS spectra of astrocytoma tissues prior to preprocessing.
Figure 7B:
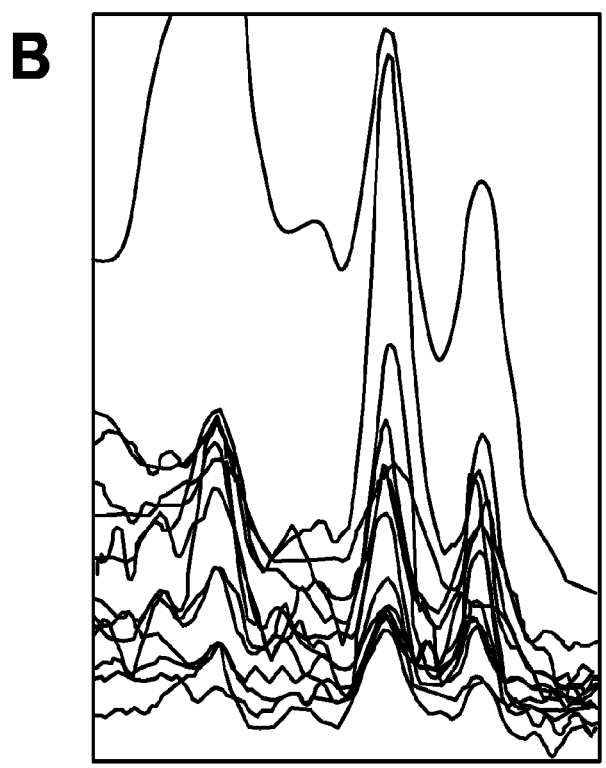
FIG. 7B is a graph comparing fourteen MRS spectra of astrocytoma tissues after chemical shift recalibration.

As a non-limiting illustrative example, FIG. 7A and FIG. 7B show an overlay of 13 MRS scans before and after recalibration, respectively. In this example, the recalibration of the MRS scans was performed based on two reference signal peaks identified by inspection of the MRS scans by an expert practitioner.

Variance-Weighting Module

Figure 8:
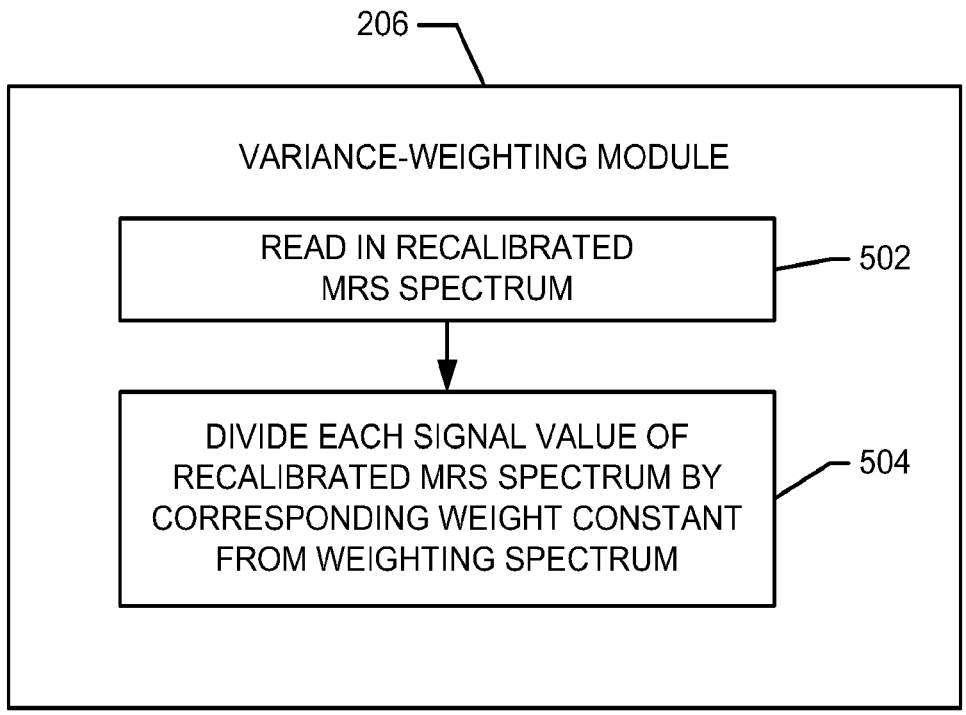
FIG. 8 is a flow chart of the processes of a variance-weighting module in a non-limiting exemplary embodiment of an MRS preprocessing system.

Referring to FIG. 8, a flow chart illustrates the operation of a non-limiting exemplary embodiment of a variance-weighting module 206 that may emphasize consistent signal peaks and depress chemical noise in an MRS spectrum. At step 502, the variance-weighting module 206 may access a recalibrated MRS spectrum data 212 at step 504. The variance-weighting module 206 may divide each signal value at each chemical shift in the spectrum by the weighting constant at the corresponding chemical shift from a weighting spectrum to generate the weighted MRS spectrum data 214.

A weighting spectrum, as used herein, is a table of chemical shifts and corresponding weighting constants. Alternatively, the weighting spectrum may be defined as a summary of weighted spectrum signals that includes a maximum weighted signal value. Weighting constants, as defined herein, are numerical constants used to increase or decrease the magnitude of the signal value at a given chemical shift, based on a predetermined criterion, including but not limited to the variation in signal values determined from a set of reference MRS spectrum data at the given chemical shift.

Figure 9:
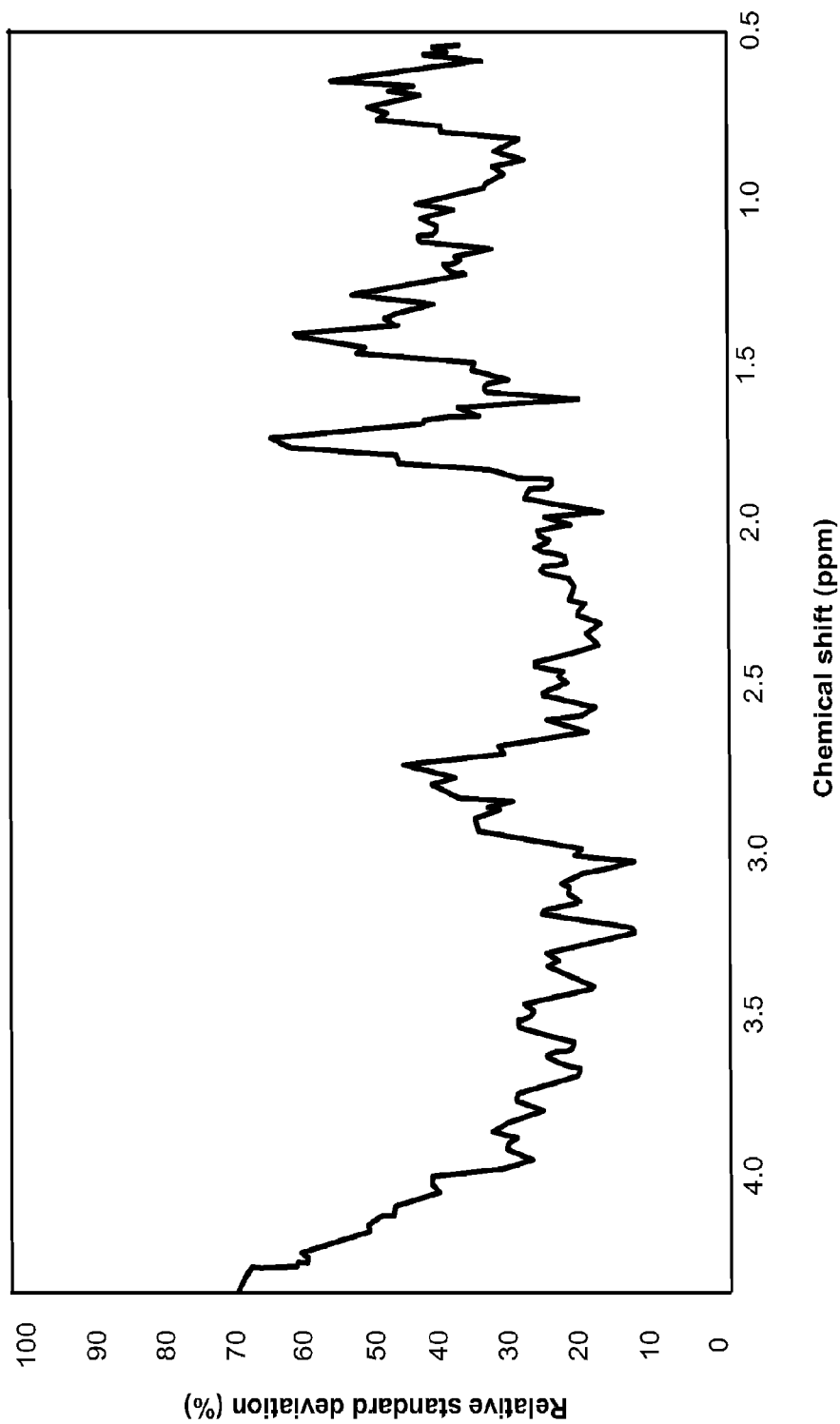
FIG. 9 is an exemplary weighting function in a non-limiting exemplary embodiment of an MRS preprocessing system.

In one non-limiting exemplary embodiment, the weighting function is the average relative standard variation determined from two or more sets of reference MRS scans, in which each set of reference scans corresponds to a particular tissue type including but not limited to normal or malignant. The two or more sets of reference MRS scans include but are not limited to raw MRS spectrum data 101, normalized MRS spectrum data 214, and recalibrated MRS spectrum data 212. As a non-limiting illustrative example, FIG. 9 shows an exemplary weighting spectrum. In this example, the relative standard deviations at each chemical shift were determined for a set of reference recalibrated MRS spectrum data 212. The relative standard deviation, as used herein, is an expression of the variation in signal values relative to the average value of the signal values for a plurality of MRS spectra data, as expressed by formula (I):

$$\text{Relative Standard Deviation} = (\text{Standard Deviation})/(\text{Average}) \times 100 \quad (I)$$

In addition, in various embodiments, the relative standard deviations may be determined for at least one other reference set of MRS data including but not limited to raw MRS spectrum data 101, normalized MRS spectrum data 214, and recalibrated MRS spectrum data 212. In various embodiments, the relative standard deviations of all reference sets may be averaged, yielding a weighting function, including but not limited to the weighting function shown in FIG. 9.

The relative standard deviation is a relatively large number for a combination of high variation, as expressed by a large standard deviation, or a relatively low overall value, as expressed by a low average. Random noise, for example, typically has a large variation around a zero value, resulting in a large relative standard deviation. Because variance weighting is implemented by dividing the signal value by the relative standard deviation, the signal value of random noise may be reduced greatly relative to the signal value of large-valued signals having relatively low variation in the reference sets of raw MRS spectra data 101.

The scaling of the MRS spectrum data performed by the variance-weighting module 206 represents a significant advancement over existing techniques such as Fisher weighting, which applies a single weighting factor consisting of the ratio of the variance within a group to the ratio of variance between groups uniformly across the signal values in the spectrum. By contrast, the variance-weighting module 206 may derive weighting factors at each individual chemical shift based on the relative standard deviation, which represents the amount of variance relative to the average value of the data. As a result, the signals most likely to contain useful diagnostic information, i.e. those signals having a high average value and low variance, are scaled up relative to random noise.

Renormalization Module

Figure 10:
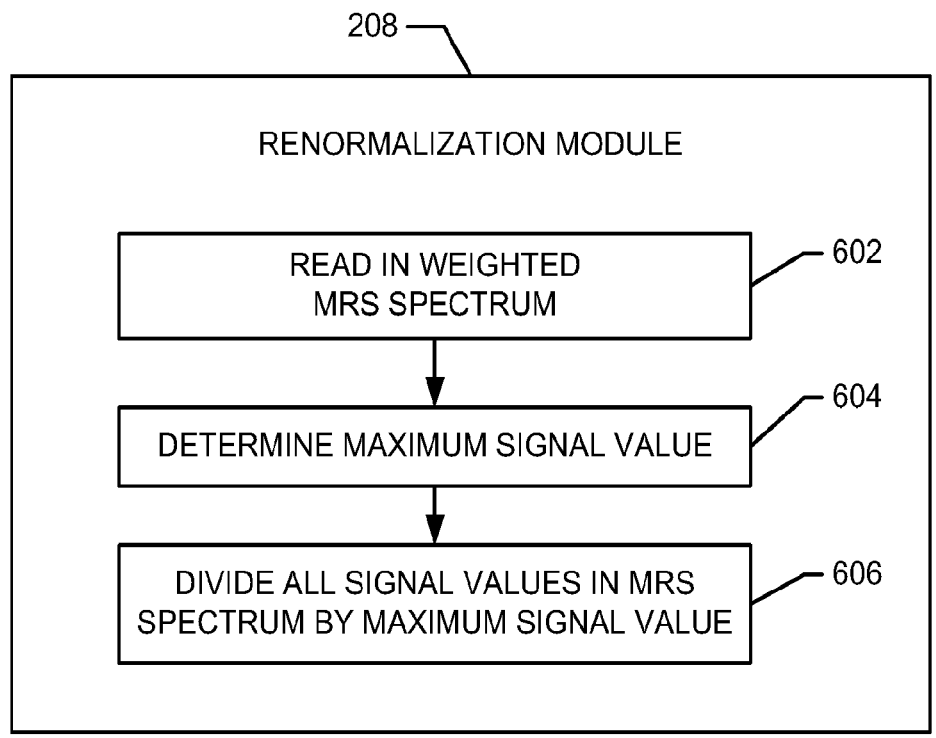
FIG. 10 is a flow chart of the processes of a renormalization module in a non-limiting exemplary embodiment of an MRS preprocessing system.

FIG. 10 is a flow chart illustrating the operation of a non-limiting exemplary embodiment of a renormalization module 208. The renormalization module 208 at step 602 may process MRS spectrum data including but not limited to scaled MRS spectrum data 214 and may transform all signal values of the spectrum to range from a normalized minimum value to a normalized maximum value. Because the scaled MRS spectrum data 214 may have been normalized by an embodiment of the normalization module 202, it may not be necessary to subtract the minimum signal value from all other signal values, since the minimum signal value may be the normalized minimum value. Instead, the maximum signal value of the scaled MRS spectrum may be determined at step 604, and all values of the MRS spectrum may be divided by this value at step 606, yielding a final preprocessed MRS spectrum data 103 that may be transferred to the output system 106 for subsequent analysis or storage in various embodiments.

System Components

MRS preprocessing system 100 may include particular components for providing various functions as discussed above. In particular, the computer readable media 104 may include volatile media, nonvolatile media, removable media, non-removable media, and/or other media or mediums that can be accessed by a general purpose or special purpose computing device. For example, computer readable media 104 may include computer storage media and communication media, including computer readable media. Computer storage media further may include volatile, nonvolatile, removable, and/or non-removable media implemented in a method or technology for storage of information, including but not limited to computer readable instructions, data structures, program modules, and/or other data. Communication media may, for example, embody computer readable instructions, data structures, program modules, algorithms, and/or other data, including as or in a modulated data signal. The communication media may be embodied in a carrier wave or other transport mechanism and may include an information delivery method. The communication media may include wired and/or wireless connections and technologies and may be used to transmit and/or receive wired or wireless communications. Combinations and/or sub-combinations of the systems, components, modules, and methods and processes described herein may be made.

The input system 102 may include, for example, a hard disk (not shown) that stores the raw MRS spectrum data 101 input files that are read by the MRS preprocessing system 100. The input system 102 also may include a storage system that stores electronic data, including but not limited to the raw MRS spectrum data 101 and other electronic data files. The input system 102 also may be one or more processing systems and/or communication systems that transmit and/or receive electronic files and/or other electronic document information or data through wireless and/or wire line communication systems, and/or other data to the MRS preprocessing system 100.

The output system 106 may include a communication system that communicates data with another system or component. The output system 106 may be a storage system that temporarily and/or permanently stores data, including but not limited to input files, intermediate data tables generated by the MRS preprocessing system 100, output files, and/or other data. The output system 106 also may include a computer, one or more processors, one or more processing systems, or one or more processes that further process data. The output system 106 may otherwise include a monitor or other display device, one or more processors, a computer, a printer, another data output device, volatile and/or nonvolatile memory, other output devices, computer readable media, a user interface 108 for displaying data, and/or a combination of the foregoing. The output system 106 may receive and/or transmit data through a wireless and/or wire line communication system. The output system 106 may be embodied by or in or operate using one or more processors or processing systems, one or more distributed or integrated systems, and/or computer readable media. The output system 106 is optional for some embodiments.

Identification of Tissue Abnormalities Using Preprocessed MRS Spectrum Data

Preprocessed MRS spectrum data 103 produced by various embodiments of the MRS preprocessing system 100 may be used to identify tissue abnormalities using a variety of methods. As one non-limiting example, an expert practitioner may visually compare the preprocessed MRS spectrum data 103 from the sample tissue to one or more comparison MRS spectrum data from tissues having known abnormalities to determine whether an abnormality is present in the sample tissue. In another non-limiting example, an automated pattern recognition algorithm may be used to automatically compare the preprocessed MRS spectrum data 103 from the sample tissue to one or more comparison MRS spectrum data from tissues having known abnormalities to determine whether an abnormality is present in a tissue.

Automated pattern recognition algorithms make use of known statistical modeling techniques including but not limited to principal component and discriminant analysis to match the signal patterns of an unknown tissue to the signal patterns within a model resulting from the analysis of the MRS signal patterns from tissues having a variety of known abnormalities. A non-limiting example of a software package that implements an automated pattern recognition method is RESolve 1.2 (Hi-Res version, Colorado School of Mines). The efficacy of any type of pattern recognition method may depend upon at least several factors including the consistency of the data analyzed.

The consistency of the MRS spectra data may depend upon at least several factors including but not limited to variation in the type of MRS instrument used to measure the MRS spectra data, the variation in operating parameters within the same MRS instrument over time, and the variation due to the practices of individual MRS technicians when measuring the MRS spectra data. The various embodiments of the MRS preprocessing system 100 may reduce much of the variation between individual MRS spectra data by performing a standardized set of processes to produce each preprocessed MRS spectrum data 103, rendering the data in a more standardized form for diagnostic purposes.

In one non-limiting exemplary embodiment, automated pattern recognition methods may be used to compare the preprocessed MRS spectrum data 103 from an unknown tissue type to a model derived from a set of entire MRS spectra data from tissues having various known abnormalities. In another embodiment, only a subset of the signals from the preprocessed MRS spectrum data 103 from an unknown tissue type corresponding to known biomarkers may be compared to a model derived from subsets of the signals of MRS spectra corresponding to the same biomarkers in tissues with known abnormalities. In this embodiment, the standardization of the MRS spectrum data made possible by the use of the MRS preprocessing system 100 results in diagnostic efficacies that are comparable to the diagnostic efficacies of pattern recognition methods that compare entire MRS spectra. Because only a discrete subset of the MRS spectra corresponding to the biomarkers are used in this embodiment, this method of identifying an unknown tissue type may be used for MRS spectra data obtained for a variety of spectra resolutions. As a result, this method may be used in a wide variety of laboratory and clinical settings equipped with MRS devices of varying resolution. In addition, because this method is resolution-independent, the standardized MRS spectra data from one or more laboratory or clinical facilities may be shared and/or combined as needed. A non-limiting example of a subset of the signals from the preprocessed MRS spectrum data is provided in Table 2 in the Examples below.

The preprocessed MRS spectrum data 103 may be derived from any tissue sample capable of measurement by an MRS device without limit. Non-limiting examples of tissue samples that may analyzed using various embodiments include brain tissue, prostate tissue, breast tissue, liver tissue, lung tissue, ovarian tissue, testicular tissue, bladder tissue, tongue tissue, dermal tissue, epidermal tissue, joint tissue, bone tissue, eye tissue, and kidney tissue. In addition, non-limiting examples of tissue abnormalities that may be identified using various embodiments include malignancy, necrosis, neurotoxicity, delamination, hypertrophy, hypotrophy, inflammation, and rheumatism.

In one illustrative non-limiting example, an embodiment of the method for detecting a tissue abnormality may be used to identify whether an unknown brain tissue sample possesses an abnormality including but not limited to necrosis, metastasized carcinoma, metastasized melanoma, demyelination, astrocytoma, oligodendroglioma, meningioma, glioblastoma multiforme, or ganglioglioma. In this example, an automated pattern recognition method may be used to match the MRS spectrum pattern of the unknown tissue sample to the model that relates the pattern of a MRS spectrum to each of the possible tissue abnormalities, as well as to the MRS spectrum pattern of normal brain tissue.

In another illustrative non-limiting example, an embodiment of the method for detecting a tissue abnormality may be used to determine the stage of a particular cancerous tissue. In this example, an automated pattern recognition method may be used to match the MRS spectrum pattern of the unknown cancerous tissue sample to the model that relates the pattern of a MRS spectrum to each of the possible cancer stages, as well as to the MRS spectrum pattern of normal non-cancerous tissue.

Other non-limiting examples of applications of the MRS preprocessing system 100 are provided in the Examples below.

Exemplary Embodiments

Figure 11:
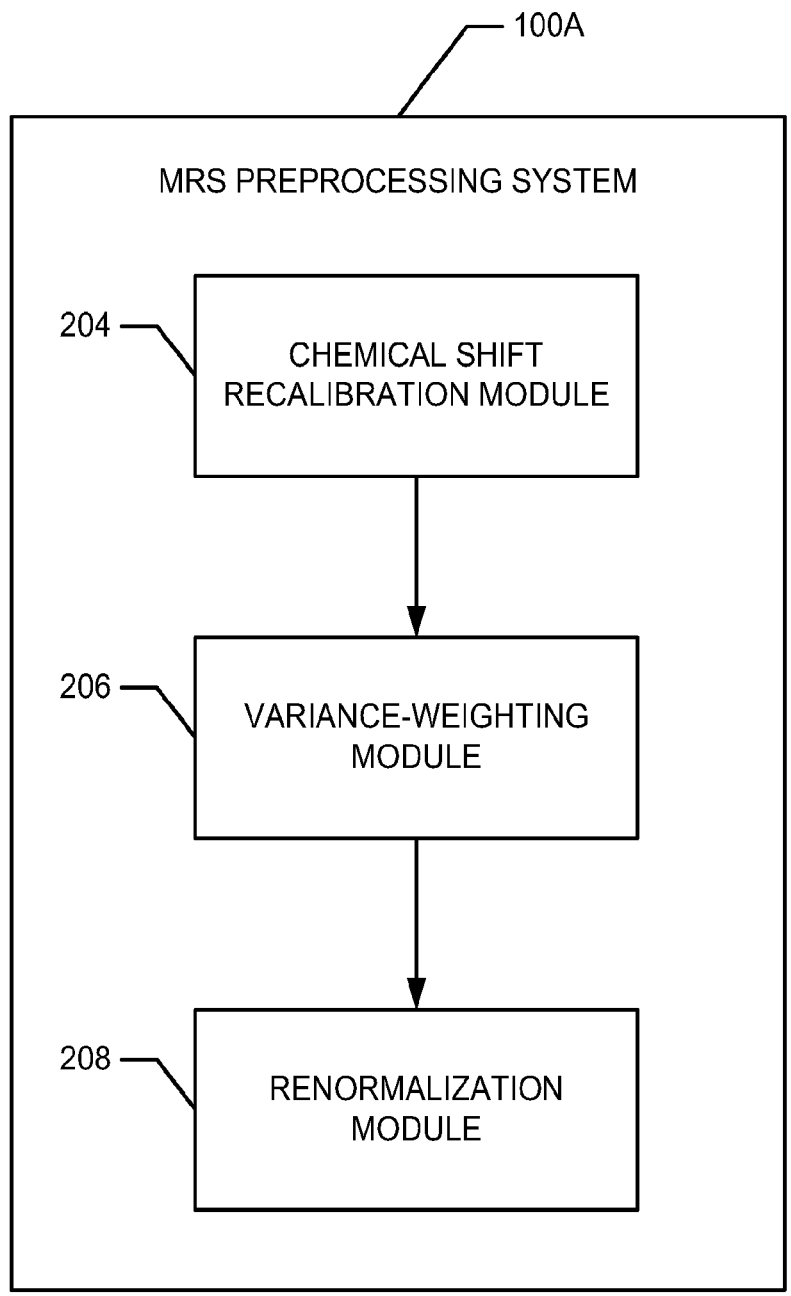
FIG. 11 is a block diagram of an MRS preprocessing system in a non-limiting exemplary embodiment of an MRS preprocessing system.

FIG. 11 is a block diagram showing a second non-limiting exemplary embodiment of the MRS preprocessing system 100A that preprocesses a normalized MRS spectrum data 210. In this embodiment, the MRS preprocessing system 100A includes a chemical shift recalibration module 204 that may recalibrate the normalized MRS spectrum data 210, a variance-weighting module 206 that may scale the recalibrated MRS spectrum data 212 at each chemical shift up or down according to a predetermined weighting function to generate a variance-weighted MRS spectrum data 214 and a renormalization module 208 that may normalize the variance-weighted MRS spectrum data 214 to produce a preprocessed MRS spectrum 103.

Figure 12:
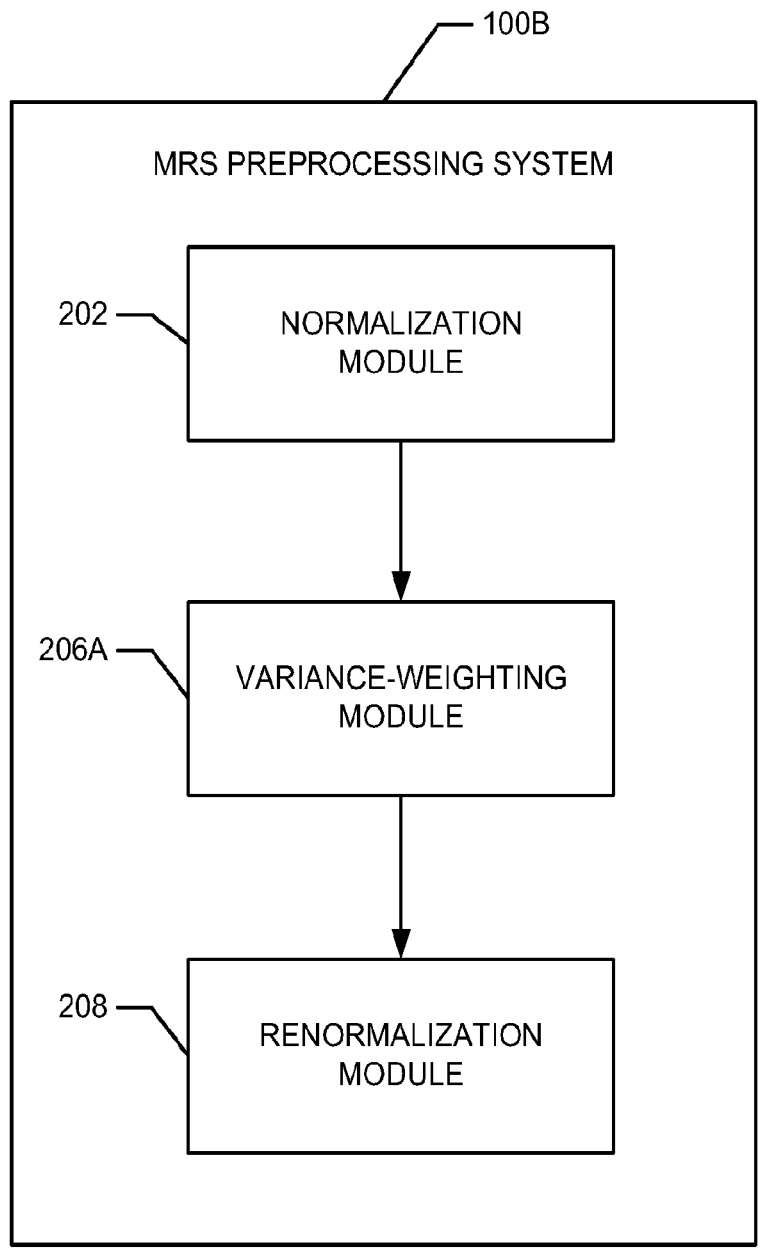
FIG. 12 is a block diagram of an MRS preprocessing system in a non-limiting exemplary embodiment of an MRS preprocessing system.

FIG. 12 is a block diagram showing a third non-limiting exemplary embodiment of the MRS preprocessing system 100B that preprocesses raw MRS spectrum data 101. In this embodiment, the MRS preprocessing system 100B may include a normalization module 202 to normalize the raw MRS spectrum data 101, a variance-weighting module 208A that may scale the recalibrated MRS spectrum data 212 at each chemical shift of the normalized MRS spectrum data 210, and a renormalization module 208 to normalize the variance-weighted MRS spectrum data 214, resulting in a preprocessed MRS spectrum data 103. This particular embodiment does not include a chemical shift calibration module 204, which simplifies the implementation of the MRS preprocessing system 100A at the cost of somewhat lower diagnostic efficacy, as presented in the examples below. This embodiment may be suitable for an initial diagnostic procedure for patients with unidentified abnormalities on traditional MR imaging. Once a possible disease state is identified using this simplified embodiment, the raw MRS spectrum data 101 could be preprocessed using an embodiment that includes a chemical shift recalibration module 204 and analyzed using a more accurate predictive diagnostic model.

Figure 13:
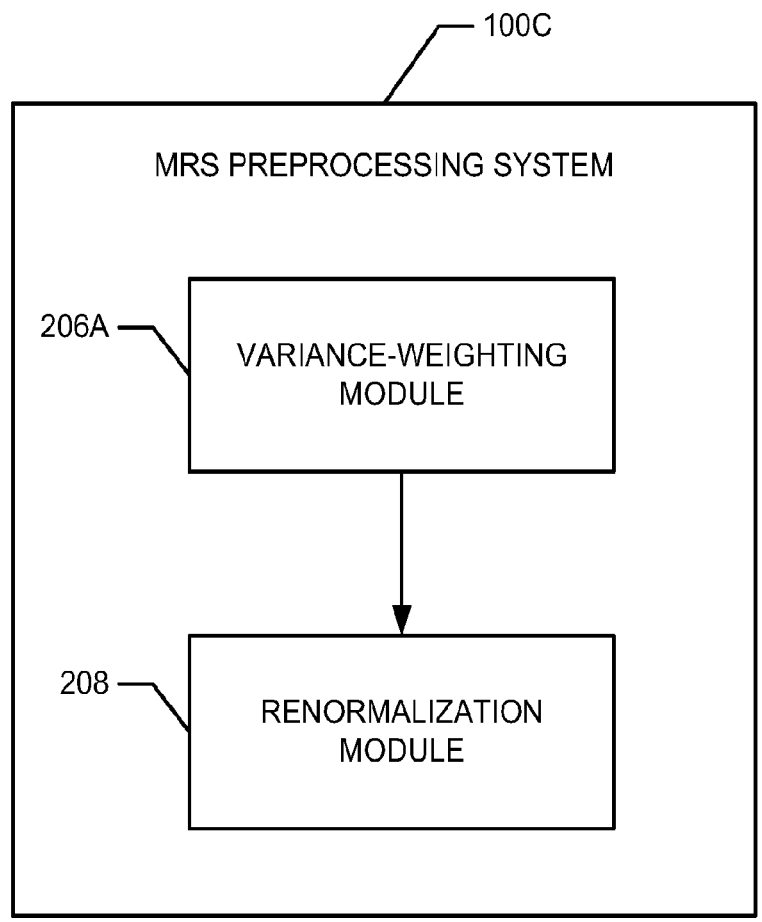
FIG. 13 is a block diagram of an MRS preprocessing system in a non-limiting exemplary embodiment of an MRS preprocessing system.

FIG. 13 is a block diagram showing a fourth non-limiting exemplary embodiment of the MRS preprocessing system 100C that preprocesses a normalized MRS spectrum data 210. In this embodiment, the MRS preprocessing system 100B may include a variance-weighting module 206A that processes the normalized MRS spectrum data 210 and may scale the normalized MRS spectrum data 210 using the variance-based weighting function previously discussed above. The resulting scaled MRS spectrum data 214 may be normalized by the renormalization module 208 to generate a preprocessed MRS spectrum data 103, which may be optionally transferred to the output system 106 for storage or subsequent analysis.

Other non-limiting exemplary embodiments may exclude the normalization module 202 and/or the renormalization module 208. Yet other non-limiting exemplary embodiments may perform the operations of any combination of embodiments of the normalization module 202, chemical shift recalibration module 204, variance-weighting module 206A, renormalization module 208 or any subset thereof in any order.

Diagnostic Applications

The preprocessing of MRS spectra as described herein results in MRS spectra of sufficient quality to develop diagnostic models to identify a wide variety of different tissue types. Although the chemical shift peaks corresponding to particular biomarkers used in the preprocessing method may vary depending upon the particular tissue to be diagnosed, the preprocessing methodology is generally applicable. Non-limiting examples of diagnostic models that may be developed using the preprocessed MRS spectra data are summarized in Table 1:

TABLE 1

Application of Diagnostic Models Using Pre-processed MRS Spectra

| Diagnostic Application | Diagnostic Value |
| --- | --- |
| Identify glioblastoma multiforme vs. necrotic tissue | Establish need for follow-up therapy |
| Discriminate astrocytoma tissue grades 2/3/4 | Intervention vs. watchful waiting |
| Identify deep brain (basal ganglia and brainstem) anomalies | Improved diagnostic efficacy; biopsy-based yield is non-diagnostic |
| Diagnosis of metastatic tumor | Origin of primary tumor unknown |
| Monitor brain trauma tissue | Need early correlation to eventual clinical outcome (return to activity, symptom duration) |
| WHO CNS Tumor Classification System | Improved definition of prognosis |
| Lymphoma differential diagnosis (lymphoma vs. glial neoplasm) | Define treatment options; non-surgical intervention is better for lymphomas |
| Identify tumor tissue | Early diagnosis; define treatment options |
| Identify tumor tissue type - glioblastoma multiforme, metastasis, or abscess | Define treatment options |
| Differential diagnosis of oligodendroglioma tissue grades | Define treatment options |
| Differentiate early Alzheimer's disease vs. mild cognitive impairment vs. vascular dementia | difficult at early stages; defines treatment options |
| Parkinson's disease vs. secondary Parkinson's disease vs. multiple system atrophy vs. corticobasil degeneration | Early diagnosis; defines treatment options |
| Huntingdon's Disease diagnosis | Early diagnosis; defines treatment options |
| Human Prion Disease diagnosis (Creutzfeldt-Jakob disease, Gerstmann-Sträussler-Scheinker syndrome, fatal familial insomnia, variant Creutzfeldt-Jakob disease, iatrogenic Creutzfeldt-Jakob disease, kuru) | Early diagnosis; defines treatment options |
| Amyotrophic lateral sclerosis diagnosis | Early diagnosis and staging; defines treatment options |
| Repeated Brain Injury | predict recovery or long term cognitive defect |
| Breast Cancer vs. benign tissues | Determine temporal window for reinjury; predict responder vs. non-responder; predict metastasis to lymph nodes |
| Diagnosis of other cancers (ovarian, prostate, bone, lung, pancreatic, colon) | Early diagnosis; defines treatment options |
| Diagnose arthritis and other joint diseases | Early diagnosis; defines treatment options |
| Diagnose any disease state using measured changes in composition or concentrations of biological components within any tissue; gout, arterial plaque, nephritis, high blood sugar, and many others | Early diagnosis; defines treatment options |

EXAMPLES

The following examples illustrate various aspects of the embodiments.

Example 1

Qualitative Effects of Chemical Shift Recalibration on MRS Spectra

To assess the qualitative effects of various preprocessing techniques on the quality of MRS spectra data from various tissue types, the following experiment was conducted.

Multiple MRS brain scans associated with nine common brain disease categories and representative normal brain tissue were obtained with institutional approval (UAMS Human Research Advisory Committee, University of Arkansas Medical Sciences Assurance M-1451, IORG0000345). The number of MRS scans obtained in each sample class are summarized in Table 2:

TABLE 2

MRS Scans Used in Preprocessing Assessment Studies

| | Scans | | |
| --- | --- | --- | --- |
| Sample Class | Used for Model Training | Used for External Validation | Total |
| Normal (N) | 20 | 41 | 61 |
| Necrosis (X) | 2 | 0 | 2 |
| Metastasized Carcinoma (C) | 6 | 0 | 6 |
| Metastasized Melanoma (Z) | 2 | 0 | 2 |
| Demyelination (D) | 3 | 0 | 3 |
| Astrocvtoma (A) | 14 | 0 | 14 |
| Oligodendroglioma (O) | 20 | 4 | 24 |
| Meningioma (M) | 3 | 0 | 3 |
| Glioblastoma multiforme (G) | 20 | 2 | 22 |
| Ganglioglioma (Z) | 2 | 0 | 2 |

All MRS spectra data were collected at the University of Arkansas for Medical Sciences (UAMS) using three GE Signa 1.5 Tesla MRIs (Echospeed clinical model LX, GE Medical Systems, Waukesha, Minn., USA) and GE's double spin echo sequence (PROBE-P). Data were acquired using repetition times of either 1400, 1500, or 2000 ms and echo times (TEs) of 35 or 144 ms. All scans were acquired as an extension of the clinical imaging services performed for these patients or from healthy volunteers.

With the exception of contralateral brain scans, the identities of training set scans were confirmed by biopsy. Contralateral scans were assumed to be normal based on the absence of any MRI-detectable anomaly.

The TE 35 ms data included signals from molecules with fairly short T2 times, including lipids, myo-inositol (MI), glutamine, glutamate, and other amino acids from N-acetyl aspartate (NAA), creatine (Cr), and choline (Cho). In addition, because the TE 35 ms data are also susceptible to water suppression artifacts, these scans may also have contained signals from macromolecules. By contrast, the TE 144 ms data contained only signals from NAA, Cr, Cho, and in some cases lactate (Lac).

All data were processed using GE SA/GE software with zero-filling to 4096 points, 2 Hz exponential line broadening, and automatic phasing using the water peak (Webb et al., 1994). Uncorrected MRS spectra data were saved as ASCII files in (ppm, signal intensity) pairs using a proprietary modification to the SA/GE software. A pathological diagnosis was appended to each MRS spectrum file. Spectral samples were blind-coded to protect patient identity and sent to the National Center for Toxicological Research for analysis.

For the chemical shift re-calibration, 97 potential chemical shift locations associated with biomarkers from high-grade glioma biopsies (Martinez-Bisbal et al, 2004) were considered. The 97 potential chemical shift locations are shown superimposed on a typical MRS scan of astrocytoma tissue in FIG. 6, and the individual biomarkers considered for this experiment are summarized in Table 3:

TABLE 3

Chemical Shifts of Potential Brain Anomaly Biomarkers

| Chemical Shift (ppm) | Biomarker |
|---|---|
| 0.90 | Fatty acids |
| 0.94 | Isoleucine |
| 0.95 | Leucine |
| 0.96 | Leucine |
| 0.98 | Valine |
| 1.00 | Isoleucine |
| 1.04 | Valine |
| 1.25 | Isoleucine |
| 1.09 | Fatty acids |
| 1.30 | Fatty acids |
| 1.33 | Lactate, Threonine |
| 1.36 | Fatty acids |
| 1.46 | Isoleucine, Lysine |
| 1.47 | Alanine |
| 1.59 | Fatty acids |
| 1.67 | Arginine |
| 1.69 | Lysine |
| 1.71 | Leucine |
| 1.72 | Arginine |
| 1.90 | γ-Aminobuturic acid, Lysine |
| 1.91 | Acetate |
| 1.97 | Isoleucine |
| 2.00 | Proline |
| 2.03 | N-acetyl aspartate |
| 2.04 | Glutamate |
| 2.03 | Fatty acids |
| 2.06 | Proline |
| 2.11 | Glutamate |
| 2.12 | Methionine |
| 2.14 | Glutamine |
| 2.19 | Methionine |
| 2.25 | Fatty acids |
| 2.27 | γ-aminobutyric acid |
| 2.28 | Valine |
| 2.34 | Glutamate |
| 2.36 | Proline |
| 2.39 | Succinate, Malate |
| 2.44 | Glutamine |
| 2.49 | N-acetyl aspartate |
| 2.63 | Methionine |
| 2.65 | Aspartic acid |
| 2.68 | N-acetyl aspartate, Malate |
| 2.80 | Aspartic acid |
| 2.82 | Fatty Acids |
| 2.86 | Asparagine |
| 2.96 | Asparagine |
| 3.01 | γ-Aminobuturic acid, Lysine |
| 3.03 | Creatine |
| 3.05 | Lysine |
| 3.06 | Tyrosine |
| 3.12 | Ethanolamine, Phenylalanine |
| 3.19 | Cholina, Tyrosina |
| 3.20 | Phosphocholine |
| 3.22 | Arginine |
| 3.23 | Glycerophosphocholine |
| 3.24 | MI |
| 3.26 | Taurine |

TABLE 3-continued

Chemical Shifts of Potential Brain Anomaly Biomarkers

| Chemical Shift (ppm) | Biomarker |
|---|---|
| 3.30 | Phenylalanine |
| 3.34 | Proline |
| 3.40 | α-Glucose |
| 3.42 | β-Glucose, Taurine, Proline |
| 3.46 | β-Glucose |
| 3.49 | β-Glucose |
| 3.52 | Choline |
| 3.53 | ml |
| 3.55 | Glycine |
| 3.56 | Glycerol |
| 3.57 | Phosphocholine |
| 3.58 | Threonine |
| 3.61 | Valine, ml |
| 3.64 | Glycerol |
| 3.67 | Glycerophosphocholine, isoleucine |
| 3.69 | α-Glucose |
| 3.72 | β-Glucose |
| 3.74 | Leucine |
| 3.75 | Glutamate |
| 3.76 | Glutamine |
| 3.77 | Lysine, Alanine |
| 3.78 | α-Glucose |
| 3.79 | Ethanolamine, Glycerol |
| 3.83 | α-Glucose, Serine |
| 3.85 | Methionine |
| 3.87 | Arginine |
| 3.89 | Aspartic Acid |
| 3.90 | β-Glucose |
| 3.93 | Creatine, Tyrosine |
| 3.94 | Serine |
| 3.97 | Serine |
| 3.99 | Asparagine |
| 4.00 | Phenylalanine |
| 4.05 | MI |
| 4.06 | Choline |
| 4.11 | Lactate |
| 4.12 | Proline |
| 4.18 | Phosphocholine |
| 4.25 | Threonine |
| 4.28 | Glycerophosphocholine |

For re-calibration, two manually identified reference proton MRS peaks were chosen based on the criteria that the MRS peaks were strongly expressed and far apart from one another within a spectrum. Appropriate references biomarker peaks varied on a case-by-case basis. Besides proximity to an expected location, the identity of a useful reference peak was sometimes inferred from its part in a pattern of adjacent peaks from unrelated molecules. This selection strategy was used successfully within groups of MRS spectra from the same lesion class. Identification of reference peaks was also inferred in some cases by the location and intensity of strong peaks resulting from other protons in the same biomarker molecule.

Using the chosen reference peaks and custom-designed recalibration/binning software to facilitate operations, each MRS spectrum was translated and re-calibrated. The software moved the selected reference peaks from their observed chemical shifts to their respective reference locations. The software also linearly interpolated all other data points in the MRS spectrum to new positions to generate the re-calibrated spectrum data.

A consistent trend in the reference peak assignments relative to the location of the corresponding peak in a spectrum was observed. At both ends of the MRS spectrum the necessary peak location shift was in the same direction and almost the same distance but the re-calibration shift required in the low ppm domain was slightly less than the shift at the high ppm end. The gross similarity in the magnitude of the required shift supported the hypothesis that the need for re-calibration arose from a phenomenon including but not limited to magnetic field strength variation as a function of tumor depth, a phenomenon that had a parallel effect on all protons within a voxel. The difference in relative correction scale with chemical shift highlighted the necessity of at least a two-point recalibration with interpolation to recalibrate the MRS spectrum.

The effectiveness of re-calibration is depicted qualitatively in FIGS. 7A and 7B, which shows a selected region of raw astrocytoma scans prior to and after recalibration respectively.

Example 2

Qualitative Effects of Variance Weighting on MRS Spectra

To assess the qualitative effects of variance weighting techniques on the quality of MRS spectra from various tissue types, the following experiment was conducted.

The MRS scan data sets described in Example 1 were preprocessed using a weighting scheme based on spectra consistency. The spectra intensities from the MRS scans were weighted to reduce random variation (noise) relative to the signal peaks from biomarkers that consistently appeared in the scans. One goal of the weighting was to increase the peak resolution and available information content of MRS without biasing tissue classification results.

To determine the weighting function, recalibrated spectra determined using the methods of Example 1 were used to ensure that biomarker peaks would occur at consistent locations on the chemical shift axis of each spectrum. In each tissue class, the relative standard deviation (RSD) was calculated for each chemical shift data point using the signal values from all spectra within each tissue class. This process yielded an RSD variance spectrum across the chemical shift domain for each class.

The average of all RSD variance spectra from all classes at each chemical shift was then determined, resulting in a single spectrum of weighting factors. This weighting function, when divided into an MRS spectrum, would not bias the determination of tissue class identity using pattern recognition techniques, but would discriminate against spectrum regions associated with chemical noise relative to those in which a peak might appear.

FIG. 9 shows a summary of the overall average Relative Standard Deviations (RSDs) as a function of proton chemical shift. These values were used as divisors to scale the MRS spectra at each respective chemical shift. The largest average RSDs appear as peaks in FIG. 9, representing chemical shift locations that had relatively high variance in signal values, but were not consistently associated with MRS peaks or proton NMR biomarkers of brain tissue. When used as a sequence of divisors in a weighting process, relatively high average RSD values in the weighting spectrum attenuate the signal values and relative low RSD values inflate the original MRS intensities at their respective chemical shift locations.

Variance weighting substantially increased the resolution of peaks in the MRS scans and produced distinguishable peaks in scans where previously the peaks had been barely observable. Further, variance weighting eliminated any remaining chemical shift variation and positioned most biomarker peaks at their expected locations. Provisionally identified biomarker peaks (Martinez-Bisbal el al, 2004) that appeared exactly at previously reported positions in this experiment included acetate (1.91 ppm); proline (2.00 ppm); glutamate (2.04 ppm); glutamine (2.14 ppm); valine (2.28 ppm); succinate and malate (2.39); N-acetyl aspartate (2.49 ppm); choline (3.19 ppm); ethanolamine, phenylalanine (3.12 ppm); taurine (3.26 ppm); β-glucose, taurine, and proline (3.42 ppm); β-glucose (3.46 ppm); and glycerol (3.46 ppm). Further, the weighting process preserved the relative peak intensity pattern associated with astrocytomas even though the weighting function was based on RSDs averaged for spectra of all available tissue types.

Example 3

Effects of MRS Spectrum Preprocessing on the Efficacy of Automated Diagnostic Methods To assess the effects of MRS spectrum preprocessing on the efficacy of automated pattern recognition methods used to identify different tissue types based on patterns of biomarker peaks, the following experiment was conducted.

MRS scans obtained using the methods described in Example 1 were preprocessed and analyzed using automated pattern recognition techniques. Three preprocessing strategies were investigated in this experiment: 1) chemical shift re-calibration, 2) baseline correction, and 3) variance-weighting. Only the TE 35 ms scans were used for preprocessing evaluations.

The effectiveness of the preprocessing strategies on the diagnostic efficacy of the MRS spectra was assessed by comparing diagnostic results calculated using RESolve 1.2 (Hi-Res version) obtained from the Colorado School of Mines. A subset of the 92 MRS scans described in Table 2 of Example 1 was used for modeling and cross-validation experiments. The RESolve software provides several alternative types of pattern recognition; in this experiment, Principal Component and Discriminant Analysis was used to develop quantitative results. The 47 MRS scans omitted from the original MRS scan data set were used subsequently as an external validation set for comparing the two methods determined to yield the highest diagnostic efficacy.

Figure 14:
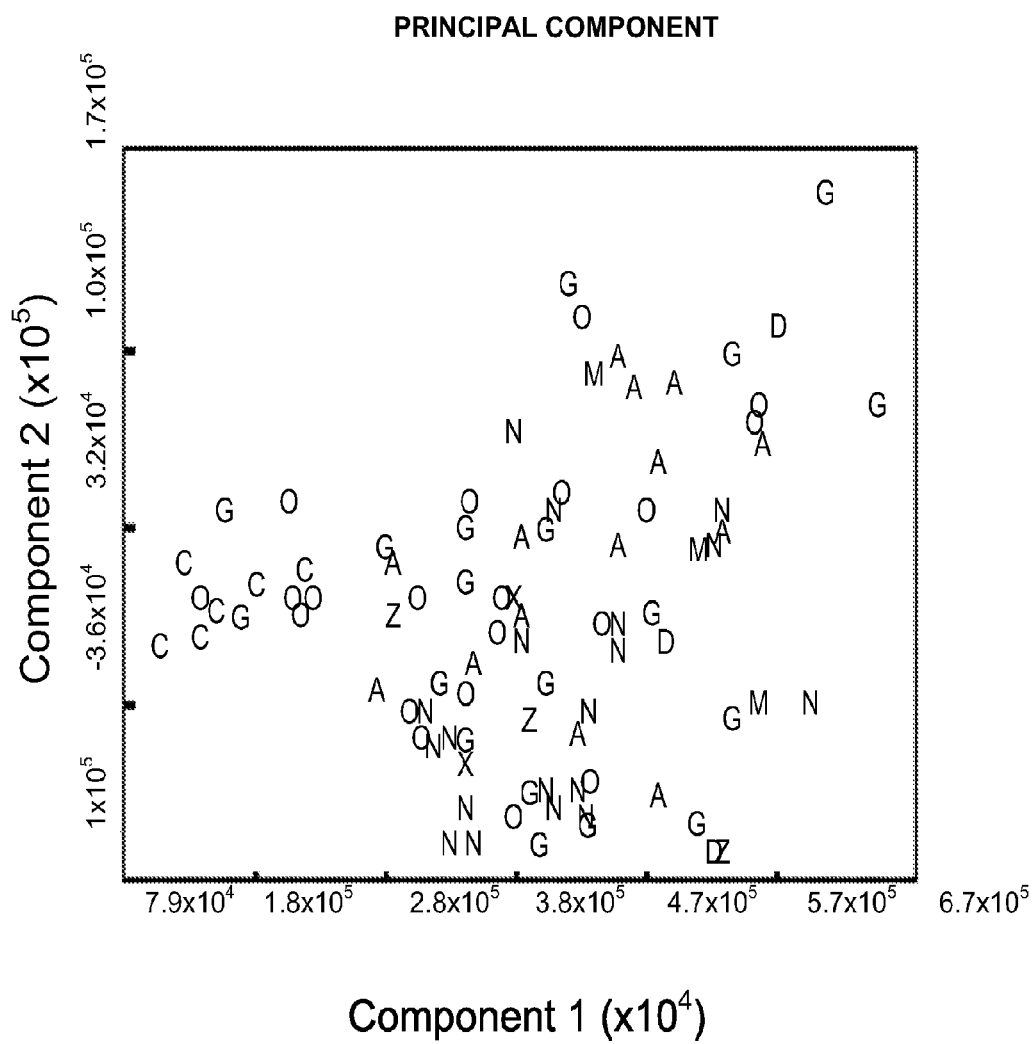
FIG. 14 is a graph summarizing the results of a principal components analysis of normalized, but otherwise not preprocessed MRS spectra.
Figure 15:
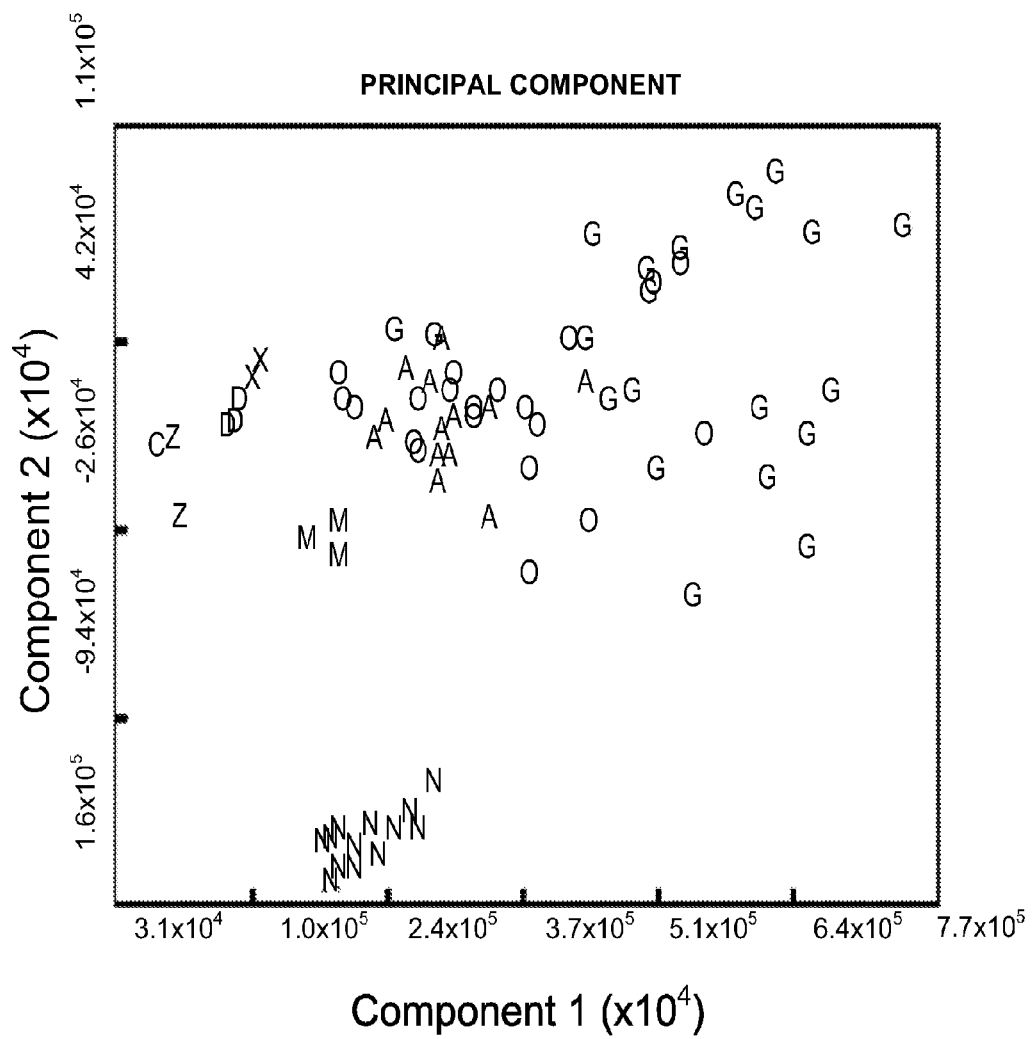
FIG. 15 is a graph summarizing the results of a principal components analysis of preprocessed MRS spectra.

FIG. 14 summarizes the results of a Principal Components and Discriminant Analysis performed by the RESolve 1.2 using minimally preprocessed MRS spectra with the spectra being normalized but otherwise unmodified prior to analysis. FIG. 15 summarizes a similar analysis performed using preprocessed MRS spectra in which the spectra were subjected to normalization, recalibration, and variance-weighting prior to analysis. A comparison of FIG. 14 with FIG. 15, shows that the preprocessing of the spectra categories reduced the separation of the data within the cluster for each particular tissue type and increased the separation distance between the clusters from different tissue types, thereby indicating that the diagnostic model derived using the preprocessed spectra discriminates more distinctly between the different tissue types.

Table 4 summarizes the results of the assessment of the diagnostic efficacy of MRS spectra that were preprocessed using various combinations of preprocessing strategies. Table 4 lists the cumulative predictive accuracy for classification among nine categories of tissue types in the four 92-scan data sets under left one out (LOO) cross-validation using all 380 data points of each MRS spectrum. Variability-weighting dramatically improved the diagnostic accuracy of the MRS spectra data relative to MRS spectra that were preprocessed using only normalization or only recalibration. A combination of normalization, recalibration, and variance-weighting resulted in the highest diagnostic efficacy of any of the preprocessing strategies assessed.

TABLE 4

Diagnostic Efficacy of Pattern Recognition Methods Using Pre-Processed MRS Spectra

| Preprocessing Strategy | Cumulative Predictive Accuracy |
|---|---|
| Normalization only | 31.5% |
| Normalization + Recalibration only | 30.4% |
| Normalization + Variance Weighting + Renormalization | 89.1% |
| Normalization + Recalibration + Variance Weighting + Renormalization | 94.6% |

Example 4

Sensitivity of the Efficacy of Automated Diagnostic Methods to the Number of Spectrum Data Points in the Diagnostic Model To assess the sensitivity of the efficacy of a diagnostic model to the number of MRS spectra data points incorporated into the development of the model, the following experiment was conducted.

Two diagnostic models were constructed using the 92 MRS spectra data points that were preprocessed using normalization, recalibration, and variance-weighting, in which the nine tissue types were classified using left one out (LOO) cross-validation as described in Example 3. The first diagnostic model incorporated all 380 data points within each spectrum, as described in Example 3. The second diagnostic model incorporated a subset of 97 data points within each spectrum corresponding to the 97 biomarkers listed in Table 2 of Example 1 above.

An external validation of the diagnostic models was performed using the 47 MRS spectra reserved for the validation. The 47 spectra are listed in Table 2 of Example 1 above. All MRS spectra were subjected to preprocessing that included normalization, recalibration, and variance-weighting prior to analysis using the diagnostic models.

Figure 16:
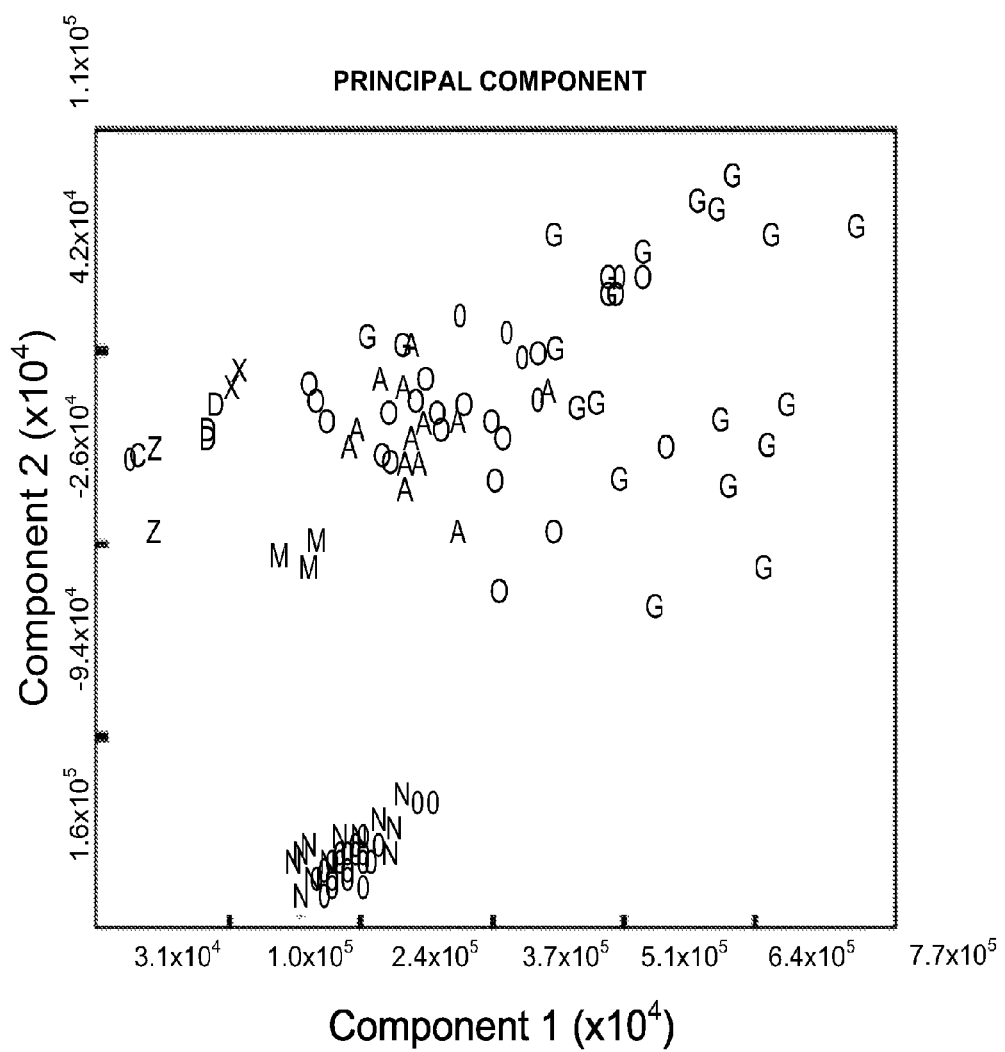
FIG. 16 is a graph summarizing the results of a principal components analysis of preprocessed MRS spectra that included external validation spectra.

FIG. 16 summarizes the results of a Principal Components analysis performed using all MRS spectra, with the 47 validation spectra shown as unknown types. As shown in FIG. 16, the 41 validation spectra obtained from normal tissue appeared to cluster tightly over the normal tissue data obtained previously. The remaining six spectra (four obtained from oligodendroglioma tissue and two obtained from glioblastoma multiforme tissue) were situated among the abnormal tissue data obtained previously.

The two data models were used to diagnose the original 92 MRS scans used to develop the models as well as the 47 validation spectra into different tissue categories. The tissue categories predicted by the diagnostic models were compared to the known classification of each spectrum to assess the accuracy of each model. The accuracy of the predicted tissue type of the two models is summarized in Table 5. The use of the diagnostic model developed using the subset of biomarker data points from the model training set resulted in a predictive accuracy of 100% for the spectra within the external validation data set, compared to 95.7% accuracy obtained using all data from the spectra.

TABLE 5

Comparison of Diagnostic Efficacy of Pattern Recognition Models Using Pre-Processed MRS Spectra

| | Cumulative Predictive Accuracy | |
|---|---|---|
| MRS Spectra Analyzed | Full Spectrum (380 data points) | Biomarker Spectrum Subset (97 data points) |
| Model Training Set (n = 92) | 94.6% | 93.5% |
| External Validation Set (n = 47) | 95.7% | 100% |

Example 5

Development of Tissue Category Subclasses Using Automated Diagnostic Methods

To assess development of an automated diagnostic method that categorized subclasses of tissue types, the following experiment was conducted.

A subset of the scans used for model training summarized in Table 2 of Example 1 were used to develop a diagnostic model using methods similar to those described in Example 3. In this experiment, only the fourteen astrocytoma scans and the 20 glioblastoma multiforme scans were used to develop the diagnostic model. The astrocytoma scans were divided into two categories corresponding to grade 2 or grade 3. The glioblastoma multiforme scans were assigned to a category corresponding to grade 4; glioblastoma multiforme is an abnormal astrocytoma tissue type also known as grade 4 astrocytoma. The diagnostic model developed using this method has an $R^2$ of 0.82.

The results of this experiment indicated that the method of developing diagnostic models using preprocessed MRS spectra may be useful in discriminating between different grades within the same tissue category.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

REFERENCES

1. Martinez-Hisbal, M. Carmen; Marti-Bonmati, Luis; Piquer, Josè; Revert, Antonio; Ferrer, Pilar; Llácer, Josi L.; Piotio, Martial; Assemat, Olivier; and Celda, Bernardo; (2004) "IH and I3C HR-MAS spectroscopy of intact biopsy samples ex vivo and in vivo 1H MRS study of human high grade gliomas", NMR Biomed. 2004; 17:191-205.
2. Webb P. B., Sailasuta N., Kohler S. J., Raidy T., Moats R. A., Hurd R. E. (1994) "Automated single-voxel proton MRS: technical development and multisite verification." Magn. Reson. Med. 31:365-373.

What is claimed is:

1. An MRS preprocessing system for preprocessing raw MRS spectrum data comprising:
   one or more processors; and
   a plurality of modules configured to be executed by the one or more processors, the plurality of modules comprising:

a normalization module to normalize the raw MRS spectrum data to generate normalized MRS spectrum data, wherein the raw MRS spectrum data comprise a summary of signals produced by a plurality of types of a tissue comprising normal and abnormal types of the tissue, at a range of nuclear magnetic resonance frequencies;

a recalibration module to shift each of the nuclear magnetic resonance frequencies representing a particular biomarker to a reference nuclear magnetic resonance frequency representing the particular biomarker to generate a recalibrated MRS spectrum data;

a variance-weighting module to scale the recalibrated MRS spectrum data by using a plurality of weighting constants to generate a weighted MRS spectrum data, wherein each of the plurality of weighting constants corresponds to a particular nuclear magnetic resonance frequency, wherein each of the plurality of weighting constants at a particular magnetic resonance frequency represents an average relative standard deviation taken from an average of raw MRS spectrum data associated with the plurality of tissue types at the particular nuclear magnetic resonance frequency, and wherein scaling the recalibrated MRS spectrum data comprises dividing each of the summary of signals from the recalibrated MRS spectrum data at the particular nuclear magnetic resonance frequency by one of the plurality of weighting constants corresponding to that same particular nuclear magnetic resonance frequency; and a renormalization module to renormalize the weighted MRS spectrum data to generate a preprocessed MRS spectrum data.

2. A non-transitory machine-readable media encoded with an MRS preprocessing system to process raw MRS spectrum data, the MRS preprocessing system comprising machine-readable instructions executable by at least one processor to perform the steps of:

receiving raw MRS spectrum data at the MRS preprocessing system executing on at least one processor, wherein the raw MRS spectrum data comprise a summary of signals produced by a plurality of types of a tissue comprising normal and abnormal types of the tissue, at a range of nuclear magnetic resonance frequencies;

normalizing the raw MRS spectrum data to generate normalized MRS spectrum data;

recalibrating the normalized MRS spectrum data;

scaling the recalibrated MRS spectrum data by using a plurality of weighting constants to generate a weighted MRS spectrum data, wherein each of the plurality of weighting constants corresponds to a particular nuclear magnetic resonance frequency, wherein the weighting constant represents an average relative standard deviation taken from an average of raw MRS spectrum data associated with the plurality of tissue types, and wherein scaling the recalibrated MRS spectrum data comprises dividing each of the summary of signals from the recalibrated MRS spectrum data at the particular nuclear magnetic resonance frequency by one of the plurality of weighting constants corresponding to that same particular nuclear magnetic resonance frequency; and renormalizing the weighted MRS spectrum data to generate a preprocessed MRS spectrum data.

3. The machine-readable media of claim 2, wherein at least one of the summary of signals at a particular nuclear magnetic resonance frequency represents a particular biomarker and at least another one of the summary of signals represents random noise.

4. The machine-readable media of claim 3, wherein scaling the normalized MRS spectrum data using the plurality of weighting constants further comprises enhancing the at least one of the summary of signals being representative of a particular biomarker relative to the at least another one of the summary of signals representative of random noise.

5. The machine-readable media of claim 2, wherein the summary of signals includes a minimum signal value and a maximum signal value, wherein each of the summary of signals for the raw MRS spectrum data is normalized by subtracting the minimum signal value from each of the summary of signals to generate a respective shifted signal, and dividing each respective shifted signal by the maximum signal value to generate the normalized MRS spectrum data.

6. The machine-readable media of claim 2, wherein recalibrating the normalized data includes shifting each of the nuclear magnetic resonance frequencies representing a particular biomarker to a reference nuclear magnetic resonance frequency representing the same particular biomarker.

7. A method for detecting a tissue abnormality in a tissue sample comprising:

(a) providing to at least one computing device a set of preprocessed comparison MRS spectrum data, wherein the preprocessed comparison MRS spectrum data is generated by (i) normalizing raw comparison MRS spectrum data comprising signals produced by each of a plurality of tissue types comprising normal and abnormal types of the tissue at a particular nuclear magnetic resonance frequency, based on the raw comparison MRS spectrum data for each of the plurality of tissue types, (ii) scaling the normalized comparison MRS spectrum data for each of the plurality of tissue types by using a weighting constant to generate a weighted comparison MRS spectrum data, wherein the weighting constant represents an average relative standard deviation taken from an average of the recalibrated comparison MRS spectrum data from the entire plurality of tissue types, and (iii) renormalizing the weighted comparison MRS spectrum data for each of the plurality of tissue types based on the raw comparison MRS spectrum data;

(b) providing to the at least one computing device preprocessed sample MRS spectrum data from the tissue sample, wherein the preprocessed sample MRS spectrum data is generated by (i) normalizing raw sample MRS spectrum data at the particular nuclear magnetic resonance frequency based on the raw sample MRS spectrum data, (ii) scaling the normalized sample MRS spectrum data by using the weighting constant to generated a weighted sample MRS spectrum data, and (iii) renormalizing the weighted sample MRS spectrum data based on the raw sample MRS spectrum data;

(c) comparing, by the at least one computing device, the preprocessed sample MRS spectrum data to the preprocessed comparison MRS spectrum data using a pattern recognition method; and (d) identifying the tissue abnormality as the known abnormality of the preprocessed comparison MRS spectrum data that most closely matches the preprocessed sample MRS spectrum data.

8. The method of claim 7, wherein the known abnormality comprises normal tissue, one or more malignant tumor tissues, one or more benign tumor tissues, or one or more non-cancerous tissue abnormalities.

* * * * *